(12) United States Patent
Fischer

(10) Patent No.: US 11,020,387 B2
(45) Date of Patent: *Jun. 1, 2021

(54) ABUSE-RESISTANT PHARMACEUTICAL COMPOSITION FOR THE TREATMENT OF OPIOID DEPENDENCE

(71) Applicant: Orexo AB, Uppsala (SE)

(72) Inventor: Andreas Fischer, Uppsala (SE)

(73) Assignee: OREXO AB, Uppsala (SE)

( * ) Notice: Subject to any disclaimer, the term of this patent is extended or adjusted under 35 U.S.C. 154(b) by 0 days.

This patent is subject to a terminal disclaimer.

(21) Appl. No.: 17/032,934

(22) Filed: Sep. 25, 2020

(65) Prior Publication Data
US 2021/0008062 A1    Jan. 14, 2021

Related U.S. Application Data

(63) Continuation of application No. 16/050,592, filed on Jul. 31, 2018, now Pat. No. 10,874,661, which is a continuation of application No. 15/499,645, filed on Apr. 27, 2017, now abandoned, which is a continuation of application No. 15/261,571, filed on Sep. 9, 2016, now abandoned, which is a continuation of application No. 14/577,823, filed on Dec. 19, 2014, now Pat. No. 9,439,900, which is a continuation of application No. 14/127,470, filed as application No. PCT/GB2012/052303 on Sep. 18, 2012, now Pat. No. 8,940,330.

(60) Provisional application No. 61/536,180, filed on Sep. 19, 2011.

(51) Int. Cl.
| | |
|---|---|
| *A61K 31/485* | (2006.01) |
| *A61K 9/14* | (2006.01) |
| *A61K 9/20* | (2006.01) |
| *A61K 9/00* | (2006.01) |
| *A61K 31/4748* | (2006.01) |

(52) U.S. Cl.
CPC ............ *A61K 31/485* (2013.01); *A61K 9/006* (2013.01); *A61K 9/0056* (2013.01); *A61K 9/14* (2013.01); *A61K 9/20* (2013.01); *A61K 9/2013* (2013.01); *A61K 9/2018* (2013.01); *A61K 9/2054* (2013.01); *A61K 9/2077* (2013.01); *A61K 9/2095* (2013.01); *A61K 31/4748* (2013.01)

(58) Field of Classification Search
None
See application file for complete search history.

(56) References Cited

U.S. PATENT DOCUMENTS

| | | |
|---|---|---|
| 4,059,686 A | 11/1977 | Tanaka et al. |
| 4,175,119 A | 11/1979 | Porter |
| 4,457,933 A | 7/1984 | Gordon et al. |
| 4,459,278 A | 7/1984 | Porter |
| 4,529,583 A | 7/1985 | Porter |
| 4,582,835 A | 4/1986 | Lewis et al. |
| 4,661,491 A | 4/1987 | Regnier |
| 4,661,492 A | 4/1987 | Lewis et al. |
| 4,755,328 A | 7/1988 | Mouton et al. |
| 4,755,386 A | 7/1988 | Hsiao et al. |
| 4,769,372 A | 9/1988 | Kreek |
| 4,885,173 A | 12/1989 | Stanley et al. |
| 4,935,428 A | 6/1990 | Lewis |
| 4,981,468 A | 1/1991 | Benfiel et al. |
| 5,069,909 A | 12/1991 | Sharma et al. |
| 5,192,802 A | 3/1993 | Rencher |
| 5,288,497 A | 2/1994 | Stanley et al. |
| 5,362,496 A | 11/1994 | Baker et al. |
| 5,547,878 A | 8/1996 | Kell |
| 5,795,909 A | 8/1998 | Shashoua et al. |
| 5,866,164 A | 2/1999 | Kuczynski et al. |
| 5,900,423 A | 5/1999 | Ward et al. |
| 6,004,582 A | 12/1999 | Faour et al. |
| 6,133,289 A | 10/2000 | Ward et al. |
| 6,217,000 B1 | 4/2001 | Younie et al. |
| 6,228,863 B1 | 5/2001 | Palermo et al. |
| 6,255,502 B1 | 7/2001 | Penkler et al. |
| 6,337,422 B1 | 1/2002 | Malthe-Sorsenssen et al. |
| 6,375,957 B1 | 4/2002 | Kaiko et al. |
| 6,440,459 B1 | 8/2002 | Stampa Diez del Corral et al. |
| 6,472,563 B1 | 10/2002 | Tanoury et al. |
| 6,656,599 B2 | 12/2003 | Grossman et al. |

(Continued)

FOREIGN PATENT DOCUMENTS

| | | |
|---|---|---|
| CN | 1943575 A | 4/2007 |
| EP | 0144243 A1 | 12/1984 |

(Continued)

OTHER PUBLICATIONS

International Search Report and Written Opinion for PCT/GB2012/052303 dated Dec. 7, 2012 (14 pages).
International Preliminary Report on Patentability for PCT/GB2012/052303 dated Oct. 15, 2013 (17 pages).
Alho, Hannu, et al., "Abuse liability of buprenorphine-naloxone tablets in untreated IV drug users", Drug and Alcohol Dependence 88, (2007), 75-78.
Ansel, H.C., et al., "Pharmaceutical Dosage Forms and Drug Delivery Systems", 7th Ed., Chapters 6-7, (1999), 164-228.

(Continued)

*Primary Examiner* — Katherine Peebles
(74) *Attorney, Agent, or Firm* — Troutman Pepper Hamilton Sanders LLP (Rochester)

(57) ABSTRACT

There is provided pharmaceutical compositions for the treatment of e.g. opioid dependency comprising microparticles of a pharmacologically-effective amount of buprenorphine, or a pharmaceutically-acceptable salt thereof, in associative admixture with particles comprising a weak acid, or particles comprising weakly-acidic buffer forming materials. The composition may further comprise a disintegrant and/or particles of a pharmacologically-effective amount of naloxone, or a pharmaceutically-acceptable salt thereof. The compositions are useful in the treatment of opioid dependency/addiction and/or pain.

14 Claims, 9 Drawing Sheets

(56) References Cited

U.S. PATENT DOCUMENTS

| | | |
|---|---|---|
| 6,696,088 B2 | 2/2004 | Oshlack et al. |
| 6,716,449 B2 | 4/2004 | Oshlack et al. |
| 6,759,059 B1 | 7/2004 | Pettersson et al. |
| 6,897,123 B2 | 5/2005 | Winther |
| 7,384,653 B2 | 6/2008 | Wright, IV et al. |
| 7,524,515 B2 | 4/2009 | Roberts |
| 7,968,021 B2 | 6/2011 | Cleary, Jr. et al. |
| 8,147,866 B2 | 4/2012 | Finn et al. |
| 8,454,996 B2 | 6/2013 | Pettersson et al. |
| 8,470,361 B2 | 6/2013 | Pettersson |
| 8,475,832 B2 | 7/2013 | Myers et al. |
| 8,658,198 B2 | 2/2014 | Pettersson |
| 8,758,664 B2 | 6/2014 | Astwood et al. |
| 8,815,911 B2 | 8/2014 | Pettersson et al. |
| 8,940,330 B2 | 1/2015 | Fischer |
| 8,980,305 B2 | 3/2015 | Pettersson |
| 9,259,421 B2 | 2/2016 | Fischer |
| 9,439,900 B2 | 9/2016 | Fischer |
| 2002/0010127 A1 | 7/2002 | Oshlack et al. |
| 2003/0004177 A1 | 1/2003 | Kao et al. |
| 2003/0035839 A1 | 2/2003 | Hirsch et al. |
| 2003/0064099 A1 | 4/2003 | Oshlack et al. |
| 2003/0068371 A1 | 4/2003 | Oshlack et al. |
| 2003/0068375 A1 | 4/2003 | Wright et al. |
| 2003/0069263 A1 | 4/2003 | Breder et al. |
| 2003/0124061 A1 | 7/2003 | Roberts |
| 2003/0124185 A1 | 7/2003 | Oshlack et al. |
| 2003/0125347 A1 | 7/2003 | Anderson et al. |
| 2003/0157168 A1 | 8/2003 | Breder et al. |
| 2003/0191147 A1 | 10/2003 | Sherman et al. |
| 2003/0220291 A1 | 11/2003 | Renshaw |
| 2004/0006091 A1 | 1/2004 | Kyle et al. |
| 2004/0180916 A1 | 9/2004 | Levine |
| 2004/0229038 A1 | 11/2004 | Cooper et al. |
| 2005/0042281 A1 | 2/2005 | Singh et al. |
| 2005/0063909 A1 | 3/2005 | Wright, IV et al. |
| 2006/0051413 A1 | 3/2006 | Chow et al. |
| 2007/0207207 A1 | 9/2007 | Tzannis et al. |
| 2008/0226717 A1 | 9/2008 | Oury et al. |
| 2009/0263476 A1 | 10/2009 | Jobdevairakkam et al. |
| 2009/0266870 A1 | 10/2009 | Yousefiani et al. |
| 2010/0129443 A1 | 5/2010 | Pettersson |
| 2010/0168147 A1 | 7/2010 | Chapleo et al. |
| 2010/0233257 A1 | 9/2010 | Herry et al. |
| 2010/0266813 A1 | 10/2010 | Matviya |
| 2011/0033541 A1 | 2/2011 | Myers et al. |
| 2011/0033542 A1 | 2/2011 | Myers et al. |
| 2011/0050265 A1 | 3/2011 | Hobbs et al. |
| 2013/0071477 A1 | 3/2013 | Fischer |

FOREIGN PATENT DOCUMENTS

| | | |
|---|---|---|
| EP | 0324725 A1 | 7/1989 |
| EP | 1201233 A1 | 5/2002 |
| EP | 0517211 B1 | 9/2004 |
| EP | 1299104 B1 | 5/2009 |
| EP | 2123275 A1 | 11/2009 |
| GB | 1428361 | 3/1976 |
| GB | 2100985 A | 1/1983 |
| GB | 2162061 A | 1/1986 |
| JP | 2007321063 A | 12/2007 |
| JP | 2010043236 A | 2/2010 |
| JP | 2011098862 A | 5/2011 |
| NO | 2001/058451 A1 | 8/2001 |
| WO | 98/48781 A1 | 11/1998 |
| WO | 0016750 A1 | 3/2000 |
| WO | 0016751 A1 | 3/2000 |
| WO | 0023079 A1 | 4/2000 |
| WO | 01/35942 A2 | 5/2001 |
| WO | 0130288 A1 | 5/2001 |
| WO | 02067903 A2 | 9/2002 |
| WO | 02/092060 A1 | 11/2002 |
| WO | 03005944 A1 | 1/2003 |
| WO | 2004067004 A1 | 8/2004 |
| WO | 2004/093801 A2 | 11/2004 |
| WO | 2005117838 A1 | 12/2005 |
| WO | 2006097361 A1 | 9/2006 |
| WO | 2006103418 A1 | 10/2006 |
| WO | 2007141328 A1 | 12/2007 |
| WO | 2008025791 A1 | 3/2008 |
| WO | 2008068471 A1 | 6/2008 |
| WO | 2008104737 A1 | 9/2008 |
| WO | 2008104738 A1 | 9/2008 |
| WO | 2008152347 | 12/2008 |
| WO | 2010132605 A1 | 11/2010 |
| WO | 2011017483 A2 | 2/2011 |
| WO | 2011017484 A2 | 2/2011 |

OTHER PUBLICATIONS

Comer, Sandra D, et al., "Abuse liability of intravenous buprenorphine/naloxone and buprenorphine alone in buprenorphine-maintained intravenous heroin abusers", Addiction 105, (2010), 709-718.

Compton, Peggy, et al., "Pharmacokinetics, Bioavailability and opioid effects of liquid versus tablet buprenorphine", Drug and Alcohol Dependence 82, (2006), 25-31.

Fudala, Paul J, et al., "Development of opioid formulations with limited diversion and abuse potential", Drug and Alcohol Dependence 83S, (2006), S40-S47.

Gennaro, A.R., "Remington: The Science and Practice of Pharmacy", 20th Ed., Chapters 45 and 46, (2000).

Harris, Debra S, et al., "Pharmacokinetics and Subjective Effects of Sublingual Buprenorphine, Alone or in Combination with Naloxone", Clin. Pharmacokinet. 43(5), (2004), 329-340.

Megarbane, Bruno, et al., "Buprenorphine is protective against the depressive effects of norbuprenorphine on ventilation", Toxicology and Applied Pharmacology 212, (2006), 256-267.

Mendelson, John, et al., "Clinical and pharmacological evaluation of buprenorphine and naloxone combinations: why the 4:1 ratio for treatment?", Drug and Alcohol Dependence 70, (2003), S29-S37.

Mohanachandran, P S, et al., "Superdisintegrants: An Overview", International Journal of Pharmaceutical Sciences Review and Research 6(1), (Jan.-Feb. 2011), 105-109.

Monte, Andrew, et al., "Diversion of Buprenorphine/Naloxone Conformulated Tablets in a Region with High Prescribing Prevalence", Journal of Addictive Diseases 28, (2009), 226-231.

Potter, Jennifer Sharpe, et al., "Pain and continued opioid use in individuals receiving buprenorphine-naloxone for opioid detoxification: Secondary analyses from the Clinical Trials Network", Journal of Substance abuse Treatment 38 (Suppl 1), (2010), S80-S86.

Schuh, Kory J, et al., "Pharmacokinetic comparison of the buprenorphine sublingual liquid and tablet", Drug and Alcohol Dependence 56, (1999), 55-60.

Sigmon, Stacey C, et al., "An injection depot formulation of buprenorphine: extended biodelivery and effects", Addiction 101, (2006), 420-432.

Smith, Meredith Y, et al., "Abuse of Buprenorphine in the United States: 2003-2005", Journal of Addictive Diseases 26(3), (2007), 107-111.

Staniforth, J N, "Ordered Mixing or Spontaneous Granulation?", Powder Technology 45, (1985), 73-77.

Stimmel, Barry, "Buprenorphine Misuse, Abuse, and Diversions: When Will We Ever Learn?", Journal of Addictive Diseases 26(3), (2007), 1-3.

Strain, Eric C, et al., "Relative bioavailability of different buprenorphine formulations under chronic dosing conditions", Drug and Alcohol Dependence 74, (2004), 37-43.

"Physicians' Desk Reference (PDR)", 56th Ed,, (2002).

Suboxone(R) product data sheet (2006).

Office Action for corresponding U.S. Appl. No. 13/622,151, dated Sep. 9, 2014.

Office Action for corresponding U.S. Appl. No. 13/802,292 dated Jan. 31, 2014.

Suboxone Rote, List (2009) (with partial translation).

Physician's Desk Reference, Product Description: Suboxone, pp. 2866-2869 (2004).

(56) References Cited

OTHER PUBLICATIONS

Handbook of Pharmaceutical Excipients, 2nd. ed., American Pharmaceutical Association, pp. 71-73, 252-261, 506-507 (1994).
Kuhlman et al., "Human Pharmacokinetics of Intravenous, Sublingual, and Buccal Buprenorphine," J. Analytical Toxicol. 20:369-378 (1996).
Declaration Under 37 C.F.R. Section 1.132 of Thomas Lundqvist, signed Jun. 5, 2007 (as filed in U.S. Appl. No. 10/851,215).
Office Action for corresponding U.S. Appl. No. 13/622,151, dated Apr. 22, 2014.
Rowe et al., Handbook of Pharmaceutical Excipients, pp. 208-210 (Crospovidone entry), pp. 581-585 (Povidone entry), 6th Edition, Pharmaceutical Press (2009).
Westerberg et al., "Physicochemical Aspects of Drug Release. IV. The Effect of Carrier Particle Properties on the Dissolution Rate from Ordered Mixtures," Internat. J. Pharm. 28:23-31 (1986).
Temgesic Rote List (1997) (English translation).
Lachman et al., "The Theory and Practice of Industrial Pharmacy," pp. 321-358, 2nd Edition, Henry Kimpton Publishers (1976).
Office Action in corresponding U.S. Appl. No. 13/622,151, dated Jul. 23, 2015.
Bell et al., "A Pilot Study of Buprenorphine-Naloxone Combination Tablet (Suboxone(R)) in Treatment of Opioid Dependence," Drug Alcohol Rev. 23:311-317 (2004).
Office Action in corresponding U.S. Appl. No. 14/127,470, dated Jul. 22, 2014.
Defendent's Preliminary Invalidity Contentions with Exhibits A-D, as served on Feb. 18, 2015, by Defendant Actavis Elizabeth LLC in C.A. No. 14-829 (D.C., Deleware).
Defendant's Final Invalidity Contentions, with Exhibits A to C, as served on Nov. 20, 2015, by Defendant Actavis Elizabeth, LLC in C.A. 14-829 (D.C. Delaware).
Westerberg et al., "Studies on Ordered Mixtures for Fast Release and Dissolution of Drugs with Low Aqueous Solubility", Doctoral thesis at Uppsala University (Department of Pharmaceutics) (1992).
Sundell-Bredenberg, S., "The Possibility of Achieving an Interactive Mixture with High Dose Homogeneity Containing an Extremely Low Proportion of a Micronised Drug," Eur. J. Pharma. Sci. 12:285-295 (2001).
Lennernas et al., "Pharmacokinetics and Tolerability of Different Doses of Fentanyl Following Sublingual Administration of a Rapidly Dissolving Tablet to Cancer Patients: A New Approach to Treatment of Incident Pain," Br. J. Clin. Pharmacol. 59(2):249-53 (2004).
Bredenberg et al., "In-Vitro Evaluation of Bioadhesion in Particulate Systems and Possible Improvement Using Interactive Mixtures," J. Pharm. and Pharmacol. 55:169-177 (2003).
Hersey, J., "Ordered Mixing: A New Concept in Powder Mixing Practice," Powder Tech. 11:41-44 (1975).
Yip et al., "Segregation in Ordered Powder Mixtures," Powder Tech. 16:149-150 (1977).
Rumpf, H., "Particle Adhesion," Agglomeration 77: Proceedings of the 2nd Int'l Symp. on Agglomeration 1:97-129 (1977).
Staniforth, J., "Order Out of Chaos," J. Pharm. Pharmacol. 39(4):329-334 (1987).
Staniforth et al., "Interparticle Forces in Binary and Ternary Ordered Powder Mixes," J. Pharm. Pharmacol. 34(3):141-145 (1982).
Wong et al., "The Effect of the Shape of Fine Particles on the Formation of Ordered Mixtures," J. Pharm. Pharmacol. 40(8):567-568 (1988).
Travers, D.,"Some Observations on the Ordered Mixing of Micronized Sodium Bicarbonate With Sucrose Crystals," Powder Tech. 12:189-190 (1975).
Kulvanich et al., "The Effect of Particle Size and Concentration on the Adhesive Characteristics of a Model Drug-Carrier Interactive System," J. Pharm. Pharmacol. 39(9):673-678 (1987).
Malmqvist et al., "Studies on Direct Compression of Tablets. VII. Sieve Methods for the Characterization of the Adhesion Tendency in Ordered Mixing," Acta Pharm. Suec. 19:437-446 (1982).

Staniforth et al., "Segregation of Vibrated Powder Mixes Containing Different Concentrations of Fine Potassium Chloride and Tablet Excipients," J. Pharm. Pharmacol. 35(9):549-554 (1983).
Zhao et al., "Functionality Comparison of 3 Classes of Superdisintegrants in Promoting Aspirin Tablet Disintegration and Dissolution," AAPS PharmSciTech 6(4):E634-E640 (2005).
Chiang et al., "Pharmacokinetics of the Combination Tablet of Buprenorphine and Naloxone," Drug & Alcohol Dependence 70:S39-S47 (2003).
Cassidy et al., Controlled Buccal Delivery of Buprenorphine, J. Controlled Release 25:21-29 (1993).
Dawson et al., Data for Biochemical Research, 3rd ed., p. 428 (1986).
Gennaro et al., eds., Remington's Pharmaceutical Sciences, 18th ed., pp. 708-717 (1990).
Food and Drug Administration—Center for Drug Evaluation and Research, "Chemistry Review(s) re Suboxone® sublingual films" USA: Food and Drug Administration, (2008).
McCormick, "Suboxone® and Subutex®," Patient Information Leaflet Food and Drug Administration, (2002).
Narang et al., "Sublingual Mucosa as a Route for Systemic Drug Delivery," International Journal of Pharmacy and Pharmaceutical Sciences, 3(2):18-22 (2011).
Kornblum et al., "A New Tablet Disintegrating Agent: Cross-Linked Polyvinylphyrrolidone," Journal of Pharmaceutical Sciences, 62(1):43-49 (1973) (cover page only).
Rowe et al., "Handbook of Pharmaceutical Excipients (Fifth Edition)," Pharmaceutical Press pp. 211-216, 701-704 (2006) ISBN: 0 85369 618 7.
Sharma et al., "Formulation and Evaluation of Fast Disintegrating Sublingual Tablets of Glipizide: An Attempt to Treat Diabetic Coma," International Journal of ChemTech Research 2(4):2026-32 (2010).
Bredenberg et al., "In Vitro and In Vivo Evaluation of a New Sublingual Tablet System for Rapid Oromucosal Absorption Using Fentanyl Citrate as the Active Substance", European Journal of Pharm. Sci. 20:327-334 (2003).
G-Biosciences, "Citric Acid (free acid), ACS Grade" Citric Acid (free acid), ACS Grade, Safety Data Sheet, (2011).
European Medicines Agency (EMEA), Scientific Discussion Paper on Suboxone®, pp. 1-42 (2006).
Marcel Dekker, Inc., "Pharmaceutical Dosage Forms" USA: Marcel Dekker, Inc. pp. 1-24(1989) ISBN: 0-8247-8044-2.
Remington, "The Science and Practice of Pharmacy," Philadelphia: Lippincott Williams and Wilkins, Ed. 20th, pp. 654-661, 858-869 (2000) ISBN: 0-683-306472.
Odou et al., "Development of Midazolam Sublingual Tablets: in vitro Study," Eur J Drug Metab Pharmacokinet, 23(2):87-91 (1998).
Expert Report of S. Craig Dyer with Exhibits 1-4, as served Dec. 21, 2015, in C.A. 14-829 (D.C. Delaware).
Allen, "Buprenorphine 2mg/ml Sublingual Drops," U.S. Pharmacist 34(2):40-41 (2009).
Staniforth, J., "Total Mixing," Int. J. Pharm Tech. & Prod Mfr. 2(1):7-12 (1981).
Hersey, J., "Preparation and Properties of Ordered Mixtures," Austral. J. Pharma. Sci. 6(1):29-31 (1977).
Travers et al., The Mixing of Micronized Sodium Bicarbonate With Sucrose Crystals, J. Pharm. Pharmacol #23 (Supp.):260S-261S (1971).
Amidon et al., "A Theoretical Basis for a Biopharmaceutic Drug Classification: The Correlation of in vitro Drug Product Dissolution and in vivo Bioavailability;" Pharmaceutical Research, 12(3):413-420 (1995).
Gandhi et al., "Oral Cavity as a Site for Bioadhesive Drug Delivery," Advanced Drug Delivery Reviews, 13:43-74 (1994).
Shojael, Amir H., "Buccal Mucosa as a Route for Systematic Drug Delivery: A Review," J. Pharm Pharmaceut. Sci, 1(1):15-30 (1998).
Leung et al., "Polyanionic Polymers in Bio-and Mucoadhesive Drug Delivery," Chapter 16, American Chemical Society, vol. 480, pp. 269-284 (1992).
Taylan et al., "Design and Evaluation of Sustained-Release and Buccal Adhesive Propranolol Hydrochloride Tablets," Journal of Controlled Release, 38:11-20 (1996).

(56) References Cited

OTHER PUBLICATIONS

Supplemental Expert Report of S. Craig Dyar Regarding Invalidity (redacted), in C.A. No. 14-829 (D.C., Delaware), served in unredacted form on Feb. 26, 2016.
U.S. Food and Drug Administration, Suboxone Film Approval Letter, Department of Health and Human Services (2010).
Hardman et al., Eds., Goodman and Gilman's The Pharmacological Basis of Therapeutics, 9th ed., pp. 548-550 (1996).
Mendelson et al., "Clinical Trials and Therapeutics: Buprenorphine and Naloxone Interactions in Opiate-Dependent Volunteers," Clinical Pharmacology & Therapeutics 60 (1):105-114 (1996).
Nath et al., "Buprenorphine Pharmacokinetics: Relative Bioavailability of Sublingual Tablet and Liquid Formulations," Journal of Clinical Pharmacology 39: 619-623 (1999).
Ponchel G., "Formulation of Oral Mucosal Drug Delivery Systems for the Systematic Delivery of Bioactive Materials," Advanced Drug Delivery Reviews 13: 75-87 (1994).
Remington, The Science and Practice of Pharmacy, Philadelphia: Lippincott Williams and Wilkens, Ed. 21st, pp. 1530, 2315 (2006).
Walsh et al., "The Clinical Pharmacology of Buprenorphine: Extrapolating from the Laboratory to the Clinic," Drug and Alcohol Dependence 70: S13-S27 (2003).
Weinberg et al., "Sublingual Absorption of Selected Opioid Analgesics," Clinical Pharmacology Therapeutics 44(3):335-342 (1988).
U.S. Pharmacopeia and National Formulary (USP28:NF23), "Buffer Solutions", pp. 2854-2855 (Jan. 1, 2005).
U.S. Pharmacopeia and National Formulary (USP34:NF29), Suppl. 2, "Buffer Solutions", pp. 5238-5239 (Dec. 1, 2011).
Sawicki et al., "Influence of Polyoxyethylene-10-Oleylether on In Vitro Verapamil Hydrochloride Penetration Through Mucous Membrane From a Model Buccal Drug Formulation," S.T.P. Pharma Sciences 8(2):107-111 (1998).
Defendant's Opening Post-trial Brief on Invalidity, as served on Jul. 15, 2016, by Defendant Actavis Elizabeth LLC in C.A. No. 14-829 (D.C., Delaware).
Office Action in Corresponding U.S. Appl. No. 14/699,889 (dated May 20, 2016).
United States Court of Appeals for the Federal Circuit, *Orexo AB, Orexo US Inc.* vs. *Actavis Elizabeth LLC*, Decision dated Sep. 10, 2018 (reversing judgment of invalidity of U.S. Pat. No. 8,940,330).
Office Action for U.S. Appl. No. 16/050,592 (dated Jun. 4, 2020).
Office Action for U.S. Appl. No. 16/050,592 (dated Nov. 22, 2019).
Lachman et al., "The Theory and Practice of Industrial Pharmacy," Lea & Febiger, 3d ed., pp. 354-356 (1986).
Defendant's Initial Invalidity Contentions with Exhibits A-E, as served on Mar. 19, 2021, by Defendants Sun Pharmaceutical Industries Limited and Sun Pharmaceutical Industries, Inc. in C.A. No. 20-cv-12588 (New Jersey).
Bredenberg, S., "New Concepts in Administration of Drug in Tablet Form: Formulation and Evaluation of a Sublingual Tablet for Rapid Absorption, and Presentation of an Individualised Dose Administration System," Comprehensive Summaries of Uppsala Dissertations from the Faculty of Pharmacy 287, pp. 1-83 (2003).
Suboxone and Subutex Prescribing Information (2005).
File History of U.S. Pat. No. 8,470,361, Amendment in Response to Non-Final Office Action, dated Oct. 18, 2012.
Decl. under 37 C.F.R. sec. 1.132 of Christer Nyström, as filed in U.S. Appl. No. 10/851,215 (dated Dec. 18, 2008).
Non-Final Office Action for U.S. Appl. No. 17/032,882 dated Feb. 19, 2021.
Sigma-Aldrich Co., Particle Size Conversion Chart [online]. Sigma-Aldrich, available online from at least Apr. 2011 [retrieved on Feb. 12, 2021]. Retrieved from the internet: https://www.sigmaaldrich.com/chemistry/stockroom-reagents/learning-center/technical-library/particle-size-conversion.html (2011).

ABUSE-RESISTANT PHARMACEUTICAL COMPOSITION FOR THE TREATMENT OF OPIOID DEPENDENCE

CROSS-REFERENCE TO RELATED APPLICATIONS

This application is a continuation of U.S. patent application Ser. No. 16/050,592, filed Jul. 31, 2018, which is a continuation of U.S. patent application Ser. No. 15/499,645, filed Apr. 27, 2017, now abandoned, which is a continuation of U.S. patent application Ser. No. 15/261,571, filed Sep. 9, 2016, now abandoned, which is a continuation of U.S. patent application Ser. No. 14/577,823, filed Dec. 19, 2014, now issued as U.S. Pat. No. 9,439,900, which is a continuation of U.S. patent application Ser. No. 14/127,470, now issued as U.S. Pat. No. 8,940,330, which is a national stage application under 35 U.S.C. § 371 of PCT Application No. PCT/GB2012/052303, filed 18 Sep. 2012, which claims the priority benefit of U.S. Provisional Application Ser. No. 61/536,180 filed 19 Sep. 2011.

This invention relates to new pharmaceutical compositions comprising opioids that are useful in the treatment of opioid/opiate dependency and/or pain, which compositions may be abuse-resistant, and may be administered transmucosally and, in particular, sublingually.

Opioids are widely used in medicine as analgesics. Indeed, it is presently accepted that, in the palliation of more severe pain, no more effective therapeutic agents exist.

Opioid agonist analgesics are used to treat moderate to severe, chronic cancer pain, often in combination with non-steroidal anti-inflammatory drugs (NSAIDs), as well as acute pain (e.g. during recovery from surgery and breakthrough pain). Further, their use is increasing in the management of chronic, non-malignant pain.

A perennial problem with potent opioid agonists however is one of abuse by drug addicts. Drug addiction is a worldwide problem of which opioid dependence, notably of heroin, is a major component. The World Health Organisation (WHO) estimates that there are approximately 4.3 million opioid addicts globally, with approximately 0.7 million in Europe and 0.3 million in the US and Canada.

Opioid dependence is a major health problem and long-term heroin use is connected to a substantially increased risk of premature death from drug overdoses, violence and suicide. Furthermore, sharing of needles among addicts contribute to the spreading of potentially fatal blood infections such as HIV, and hepatitis C. In addition, opioid dependence often leads to difficulties with social relations, inability to manage a normal job and increased criminality to finance addiction, with severe implications for the opioid dependent person and his/her family.

Opioid addicts not only feed their addition by direct purchase of opioids "on the street", typically in the form of opioid-based powders (such as heroin), but may also get hold of pharmaceutical formulations intended for the treatment of e.g. pain. Such individuals then often apply innovative techniques in their abuse of such formulations, for example by extracting a large quantity of active ingredient from that formulation into solution, which is then injected intravenously. With most commercially-available pharmaceutical formulations, this can be done relatively easily, which renders them unsafe or "abusable". Thus, there is a general need for non-abusable pharmaceutical formulations comprising opioid agonists.

Opioid addicts are often treated by way of "substitution" therapy, in which mainly "street" opioids of unknown strength and purity are replaced by pharmaceutical-grade opioids with a longer duration of action, such as buprenorphine.

Further, a new cohort of opioid-dependent individuals has begun to emerge in the last decade, particularly in the US, namely so-called "white collar" addicts, who have become dependent upon prescription opioids, typically initiated for the treatment of pain. Substitution therapy is also required for this growing group of patients.

SUMMARY OF THE INVENTION

Opioid antagonists are used to reverse the pharmacological effects of opioids. Selective opioid antagonists, such as naloxone, may therefore be used to treat narcotic drug overdose or to diagnose suspected opioid addiction. Naloxone in particular has a poor bioavailability when administered transmucosally but is rendered fully bioavailable when administered by injection.

A simple mixture combination tablet comprising the opioid partial agonist buprenorphine and naloxone in a 4:1 ratio for sublingual administration is available under the trademark Suboxone®. (This and other abuse-resistant opioid-containing formulations are reviewed by Fudula and Johnson in *Drug and Alcohol Dependence*, 83S, S40 (2006). See also US patent applications US 2003/0124061 and US 2003/0191147.)

Because of naloxone's poor transmucosal bioavailability, if Suboxone is taken sublingually, as directed, the small amount of naloxone that is absorbed should not interfere with the desired effects of buprenorphine.

On the other hand, if Suboxone is dissolved and injected by an addict with a view to achieving a "high", the increased availability of naloxone via the parenteral route should serve to antagonize the effects of buprenorphine, at the same time as precipitating unpleasant opioid withdrawal symptoms in an individual physically dependent on opioids.

Nonetheless, when administered parenterally, naloxone's functional blockade of buprenorphine's action is also only partial and is short-lived in its nature. In view of this, diversion and illicit use of Suboxone has frequently been reported, especially in hidden populations such as incarcerated and active drug abusers (see, for example, Alho et al, *Drug and Alcohol Dependence*, 88, 75 (2007), Monte et al, *Journal of Addictive Diseases*, 28, 226 (2009), Stimmel, ibid., 26, 1 (2007) and Smith et al, ibid., 26, 107, 2007). Indeed, a recent study of untreated intravenous abusers in Finland revealed that 68% reported abuse of Suboxone. Moreover, 66% of those that had abused the drug once admitted that they had abused it at least once subsequently, or even regularly thereafter (see Ahlo et al, supra).

Further, Suboxone has also been reported to have several other significant limitations. For example, the tablets are large and disintegrate slowly. The bioavailability of buprenorphine is also significantly lower than for a sublingual solution (see Compton et al, *Drug and Alcohol Dependence*, 82, 25 (2006)). Moreover, the taste is not well tolerated by all patients and the tablet has an unpleasant gritty mouthfeel. A film-based product has recently been developed to counteract these problems, but the film formulation also does not dissolve particularly quickly. Furthermore, a maximum of only two films (with doses of 2 mg and 8 mg of buprenorphine) may be administered simultaneously. Sequential administration is thus required for (commonly administered) doses in excess of 10 mg or 16 mg of buprenorphine, respectively.

There is thus a presently unmet clinical need for an abuse-resistant product for use in opioid addiction substitution therapy, but which does not possess the afore-mentioned limitations. In particular, if it were possible to devise a formulation that was capable of significantly increasing the bioavailability of buprenorphine, it might be possible to reduce the amount of this active pharmaceutical ingredient, giving rise to less opioid in the formulation and so reducing the amount available for injection if diverted by way of intravenous abuse.

International patent applications WO 00/16751, WO 2004/067004, WO 2006/103418 and WO 2008/068471 all disclose drug delivery systems for the treatment of e.g. acute pain by sublingual administration, applying an interactive mixture principle, in which the active ingredient in microparticulate form is adhered to the surfaces of larger carrier particles in the presence of a bioadhesive and/or mucoadhesive promoting agent. WO 2008/068471 in particular discloses a formulation comprising particles of opioid agonist drug upon the surfaces of carrier particles comprising an opioid antagonist, such as naloxone.

Prior art documents, including international patent applications WO 03/005944, WO 02/067903, WO 2007/141328, WO 2010/132605, WO 01/30288 and US patent application US 2009/0263476 A1 employ pH modifying agents to promote dissolution and/or absorption of active ingredients.

We have now found that, by applying a specific formulation principle to a combination of specific active ingredients, buprenorphine and naloxone, we have provided a product with unexpected, significantly improved pharmaceutical and clinical properties.

According to a first aspect of the invention there is provided a pharmaceutical composition comprising microparticles of a pharmacologically-effective amount of buprenorphine, or a pharmaceutically-acceptable salt thereof, in associative admixture with particles comprising a weak acid, or particles comprising weakly-acidic buffer forming materials. Such compositions are referred to hereinafter as "the compositions of the invention".

It is preferred that the pharmaceutical compositions comprising buprenorphine, or a pharmaceutically-acceptable salt thereof, are presented in admixture (e.g. in simple mixture) together with a disintegrant.

In this respect, there is further provided a pharmaceutical composition comprising:
(i) a composition of the invention as hereinbefore defined ("Component (i)"); and
(ii) a disintegrant (hereinafter "Component (ii)").

Compositions comprising Components (i) and (ii) are also referred to together hereinafter as compositions of the invention.

It is further preferred that the pharmaceutical compositions comprising buprenorphine, or a pharmaceutically-acceptable salt thereof, are presented in admixture (e.g. in simple mixture) together with a disintegrant and naloxone.

In this respect, there is further provided a pharmaceutical composition comprising:
(a) a composition of the invention comprising Components (i) and/or (ii) as hereinbefore defined; and
(b) particles of a pharmacologically-effective amount of naloxone, or a pharmaceutically-acceptable salt thereof (hereinafter "Component (iii)").

Compositions comprising Component (iii) formulated together with Components, (i) and/or (ii) are also referred to together hereinafter as compositions of the invention.

DETAILED DESCRIPTION OF THE INVENTION

Figure 1:
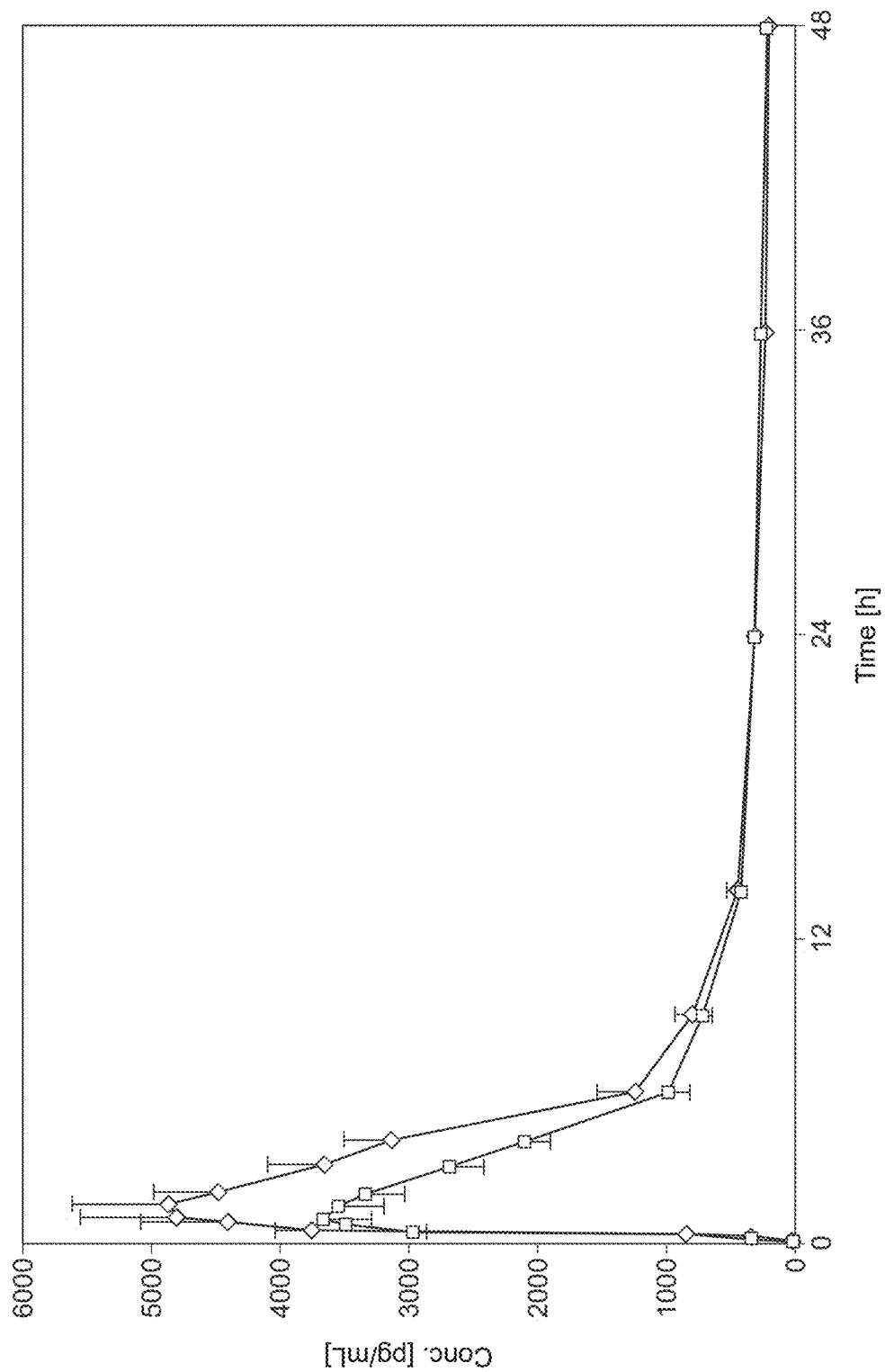
FIG. 1: Graph of plasma profile for buprenorphine according to Example 2.

Buprenorphine and pharmaceutically-acceptable salts thereof are presented in the compositions of the invention in the form of microparticles. Naloxone and pharmaceutically-acceptable salts thereof may also (e.g. preferably) be presented in compositions of the invention in the form of microparticles. Microparticles preferably possess a weight based mean diameter, number based mean diameter and/or a volume based mean diameter of between about 0.5 µm and about 15 µm, such as about 1 µm and about 10 µm. As used herein, the term "weight based mean diameter" will be understood by the skilled person to include that the average particle size is characterised and defined from a particle size distribution by weight, i.e. a distribution where the existing fraction (relative amount) in each size class is defined as the weight fraction, as obtained by e.g. sieving (e.g. wet sieving). As used herein, the term "number based mean diameter" will be understood by the skilled person to include that the average particle size is characterised and defined from a particle size distribution by number, i.e. a distribution where the existing fraction (relative amount) in each size class is defined as the number fraction, as measured by e.g. microscopy. As used herein, the term "volume based mean diameter" will be understood by the skilled person to include that the average particle size is characterised and defined from a particle size distribution by volume, i.e. a distribution where the existing fraction (relative amount) in each size class is defined as the volume fraction, as measured by e.g. laser diffraction.

Microparticles of active ingredients may be prepared by standard micronisation techniques, such as grinding, jet milling, dry milling, wet milling, precipitation, etc. An air elutriation process may be utilised subsequently to prepare specific size fractions, if required.

Preferred salts of buprenorphine and naloxone include hydrochloride salts.

Buprenorphine and pharmaceutically-acceptable salts thereof are formulated together in associative admixture with particles of a weak acid, or with particles of weakly-acidic buffer forming materials, to provide compositions of the invention (or Component (i) of compositions of the invention).

Weakly acidic materials that may be mentioned include those that, when provided in a composition of the invention, enable the provision when the composition is dissolved in water and/or saliva (e.g. at the site of administration of compositions of the invention) of a pH of between about 4.0 and about 6.5 (e.g. about 6.25), and are present in a sufficient amount to enable the maintenance of pH within this range for an appropriate length of time (e.g. about 30 seconds, such as about 1 minute) to about 3 minutes (e.g. about 2 minutes, such as about 1.5 minutes) to facilitate dissolution of, particularly, the buprenorphine microparticles, and/or absorption of buprenorphine across the sublingual mucosa thereafter. For the purpose of this invention, the term includes substances that are safe for use in mammals, and includes weak acids, weak acid derivatives and other chemicals that convert to weak acids in vivo (e.g. precursors that convert to acids in vivo, by for example being sequentially activated in accordance with properties of the local environment). Typical pKas of weak acids are in the range of between about −1.5 (e.g. about −1.74) and about 16 (e.g. about 15.74) (e.g. see Vollhardt, *Organic Chemistry* (1987). A preferred range is between about 1 and about 10. More preferably, the weakly acidic material comprises a weak acid that is safe for human consumption, for example a food acid, such as malic acid, fumaric acid, adipic acid, succinic acid, lactic acid, acetic acid, oxalic acid, maleic acid, ammonium chloride, preferably tartaric acid, and more preferably citric acid, or a combination of such acids. The skilled person will appreciate that, when weak acids are employed which are not solids (and therefore not particulate) at or around room temperature and atmospheric pressure, they may be adsorbed into a particulate carrier material (such as colloidal silica) in order to provide particles comprising the weakly acidic material.

Weakly-acidic buffer forming materials include materials that, when provided in a composition of the invention, provide a weakly acidic buffer system when the composition is dissolved in water and/or saliva (e.g. at the site of administration of compositions of the invention), enabling the provision of a pH of between about 4.0 and about 6.5 (e.g. about 6.25), and are present in a sufficient amount to enable the maintenance of pH within this range for an appropriate length of time (e.g. about 30 seconds, such as about 1 minute) to about 3 minutes (e.g. about 2 minutes, such as about 1.5 minutes) to facilitate dissolution of, particularly, the buprenorphine microparticles, and/or absorption of buprenorphine across the sublingual mucosa thereafter. Buffer forming materials thus include combinations of weak acid and salt of weak acid, such as combinations of the aforementioned acids with alkaline salts of those acids, including sodium citrate, potassium citrate, sodium tartrate, potassium tartrate and the like. Preferred buffer forming materials are citric acid and sodium citrate. The skilled person will appreciate that, when materials are employed which are not solids (and therefore not particulate) at or around room temperature and atmospheric pressure, they may be adsorbed into a particulate carrier material (such as colloidal silica) in order to provide particles comprising the weakly-acidic buffer forming materials.

Suitable particles sizes of weakly acidic, or weakly-acidic buffer forming, materials are in the range about 1 μm and about 1000 μm (e.g. about 800 μm, such as about 750 μm), and preferably between about 40 (such as about 50 μm) and about 600 μm. Suitable amounts of weakly acidic materials that enable the maintenance of pH within the aforementioned ranges after oral administration as hereinbefore described are in the range of at least about 1% to about 10% by weight of the total formulation. Suitable total amounts of weakly-acidic buffer forming materials that enable the maintenance of pH within the aforementioned ranges after oral administration as hereinbefore described are in the range of at least about 1% to about 15% by weight of the total formulation.

The disintegrant or "disintegrating agent" that may be employed as, or as part of, Component (ii) in compositions of the invention may be defined as any material that is capable of accelerating to a measurable degree the disintegration/dispersion of a composition of the invention. The disintegrant may thus provide for an in vitro disintegration time of about 30 seconds or less, as measured according to e.g. the standard United States Pharmacopeia (USP) disintegration test method (see *FDA Guidance for Industry: Orally Disintegrating Tablets*; December 2008). This may be achieved, for example, by the material being capable of swelling, wicking and/or deformation when placed in contact with water and/or mucous (e.g. saliva), thus causing tablet formulations to disintegrate when so wetted.

Suitable disintegrants (as defined in, for example, Rowe et al, *Handbook of Pharmaceutical Excipients*, $6^{th}$ ed. (2009)) include cellulose derivatives such as hydroxypropyl cellulose (HPC), low substituted HPC, methyl cellulose, ethyl hydroxyethyl cellulose, carboxymethyl cellulose calcium, carboxymethyl cellulose sodium, microcrystalline cellulose, modified cellulose gum; starch derivatives such as moderately cross-linked starch, modified starch, hydroxylpropyl starch and pregelatinized starch; and other disintegrants such as calcium alginate, sodium alginate, alginic acid, chitosan, colloidal silicon dioxide, docusate sodium, guar gum, magnesium aluminium silicate, polacrilin potassium and polyvinylpyrrolidone. Combinations of two or more disintegrants may be used.

Preferred disintegrants include so-called "superdisintegrants" (as defined in, for example, Mohanachandran et al, *International Journal of Pharmaceutical Sciences Review and Research,* 6, 105 (2011)), such as cross-linked polyvinylpyrrolidone, sodium starch glycolate and croscarmellose sodium. Combinations of two or more superdisintegrants may be used.

Disintegrants may also be combined with superdisintegrants in compositions of the invention.

Disintegrants and/or superdisintegrants are preferably employed in an (e.g. total) amount of between 0.5 and 15% by weight based upon the total weight of a composition. A preferred range is from 1 to 8%, such as from about 2 to about 7% (e.g. about 5%, such as about 4%) by weight.

Compositions of the invention may be formulated together (along with any other materials that may be present) by standard simple mixing techniques or by way of granulation.

Granules may be prepared by a process of dry granulation, wet granulation, melt granulation, thermoplastic pelletising, spray granulation or extrusion/spheronisation.

Wet granulation techniques are well known to those skilled in the art and include any technique involving the massing of a mix of dry primary powder particles using a granulating fluid, which fluid comprises a volatile, inert solvent, such as water, ethanol or isopropanol, either alone or in combination, and optionally in the presence of a binder or binding agent. The technique may involve forcing a wet mass through a sieve to produce wet granules which are then dried, preferably to a loss on drying of less than about 3% by weight.

Dry granulation techniques are also well known to those skilled in the art and include any technique in which primary powder particles are aggregated under high pressure, including slugging and roller compaction, for example as described hereinafter.

Melt granulation will be known by those skilled in the art to include any technique in which granules are obtained through the addition of a molten binder, or a solid binder which melts during the process. After granulation, the binder solidifies at room temperature. Thermoplastic pelletising will be known to be similar to melt granulation, but in which plastic properties of the binder are employed. In both processes, the agglomerates (granules) obtained comprise a matrix structure.

Spray granulation will be known by those skilled in the art to include any technique involving the drying of liquids (solutions, suspensions, melts) while simultaneously building up granulates in a fluid bed. The term thus includes processes in which foreign seeds (germs) are provided upon which granules are built up, as well as those in which inherent seeds (germs) form in the fluid bed due to abrasion and/or fracture, in addition to any spray coating granulation technique generally. The sprayed liquid coats the germs and assists further agglomeration of particles. It is then dried to form granules in the form of a matrix.

Extrusion/spheronisation will be well known to those skilled in the art to include any process involving the dry mixing of ingredients, wet massing along with a binder, extruding, spheronising the extrudate into spheroids of uniform size, and drying.

In particular, microparticles of buprenorphine or salt thereof and particles of weakly acidic, weakly-acidic buffer forming, materials are presented in associative admixture with each other in compositions of the invention. By "associative admixture" we mean that whether or not Component (i) is subsequently formulated along with Components (ii) and (iii) as hereinbefore defined, some form of mixing step (simple mixing, granulation as described hereinbefore, or otherwise) takes place as between the buprenorphine/salt microparticles and particles of weakly acidic, weakly-acidic buffer forming, materials, rendering them in intimate contact with each other.

For the avoidance of doubt, by "intimate contact", we include that microparticles of buprenorphine or salt thereof, and particles of weakly acidic, weakly-acidic buffer forming, materials, are presented in compositions of the invention in any form in which they are, at least in part, in intimate contact with each other. This includes the possibility of the inclusion of quickly dissolving coatings on one or other, or both, sets of particles.

In this respect, Component (i) is preferably presented as, or as part of, a composition of the invention in the form of a interactive mixture comprising at least one population of a carrier particles upon the surfaces of which are presented (e.g. adhered) microparticles of buprenorphine or a pharmaceutically acceptable salt thereof.

The term "interactive" mixture will be understood by those skilled in the art to include the term "ordered" mixture, and to denote a mixture in which particles do not appear as single units, as in random mixtures, but rather where smaller particles (e.g. microparticles of, for example, buprenorphine) are attached to (i.e. adhered to or associated with) the surfaces of larger carrier particles. Such mixtures are characterised by interactive forces (for example van der Waals forces, electrostatic or Coulomb forces, and/or hydrogen bonding) between carrier and surface-associated particles (see, for example, Staniforth, *Powder Technol.*, 45, 75 (1985)). In final mixtures, and compositions comprising such mixtures, the interactive forces need to be strong enough to keep the adherent particles at the carrier surface.

When interactive mixtures are employed as the formulation principle by which the particulate Component (i) is presented in a composition of the invention, these are made, preferably, with carrier particles that are of a size (weight and/or volume based average or mean diameter, vide supra) that is between about 30 µm and about 1000 µm (e.g. about 800 µm, such as about 750 µm), and preferably between about 40 (such as about 50 µm) and about 600 µm.

Carrier particles may comprise pharmaceutically-acceptable substances that are soluble in water, such as carbohydrates, e.g. sugars, such as lactose, and sugar alcohols, such as mannitol, sorbitol and xylitol; pharmaceutically-acceptable inorganic salts, such as sodium chloride. Water soluble carrier particles may also comprise the weakly acidic, and/or weakly acidic buffer forming materials, mentioned hereinbefore (such as citric acid and/or sodium citrate). Alternatively, carrier particles may comprise pharmaceutically-acceptable substances that are insoluble or sparingly soluble in water, such as dicalcium phosphate anhydrate, dicalcium phosphate dihydrate, tricalcium phosphate, calcium carbonate, and barium sulphate; starch and pre-gelatinised starch; bioadhesive and mucoadhesive materials, such as cross-linked polyvinylpyrrolidone and croscarmellose sodium; and other polymers, such as microcrystalline cellulose, cellulose and; or mixtures thereof.

By "soluble in water" we include that the material has a solubility in water that is greater than 33.3 mg/mL at atmospheric pressure (e.g. 1 bar) and room temperature (e.g. 21° C.). On the other hand, the term "sparingly soluble or insoluble in water" includes materials that have a solubility in water that is less than 33.3 mg/mL under the same conditions. Preferred soluble carrier particle materials include sugar alcohols, such as sorbitol, xylitol and particularly mannitol. Preferred sparingly water-soluble or water-insoluble carrier particle materials include cellulose and starches, such as microcrystalline cellulose.

It is preferred that buprenorphine or pharmaceutically acceptable salt thereof is presented on the surfaces of water-soluble carrier particles.

In this respect, as stated above, weakly acidic materials, and/or weakly-acidic buffer forming materials, may also function as water-soluble carrier particle materials. Therefore, the associated admixture of such materials with buprenorphine/salt thereof may mean the former comprise carrier particles upon which microparticles of the latter are presented. In such cases, such materials may be presented at least as further water-soluble carrier particles, in addition to the presence of other water-soluble carrier particles, upon the surfaces of both of which are presented burprenorphine microparticles.

When carrier particles comprise such weakly acidic/buffer forming materials, composites of such materials with other water-soluble carrier particle materials (such as those described hereinbefore) may be provided. Such materials may be prepared by direct compression or granulation, for example. Alternatively, carrier particles may consist essentially of a weakly acidic material and/or one or more materials that, when dissolved in saliva, give rise to a weakly acidic buffer system. By "consisting essentially" of such materials, we mean that, excluding the possible presence of water (vide infra), the carrier particles comprise at least about 95%, such as at least about 98%, more preferably greater than about 99%, and particularly at least about 99.5% by weight (based on the total weight of the carrier particle) of such materials. These percentages exclude the presence of trace amounts of water (e.g. crystal water or water bound to external surfaces of materials), and/or any impurities that may be present in such materials, which impurities may arise following the production of such materials, either by a commercial or non-commercial third party supplier, or by a skilled person making a composition of the invention.

Alternatively (and/or in addition), in Component (i), particles of weakly acidic material, and/or of weakly-acidic buffer forming materials, may be presented, at least in part, upon the surfaces of, and/or between, carrier particles. In such cases, suitable particle sizes of such materials are as presented herein for active ingredients and/or disintegrants.

When employed in compositions of the invention, Components (ii) and (iii) are preferably formulated together, for example to form particles comprising naloxone or salt thereof and the disintegrant, prior to mixing with Component (i). Alternatively, particles of weakly acidic material, and/or of weakly-acidic buffer forming materials, may be formulated along with Components (ii) and/or (iii) prior to mixing with buprenorphine microparticles, which latter microparticles may be presented in the form of interactive mixtures with carrier particles as hereinbefore described. Weakly acidic, and/or weakly-acidic buffer forming, materials may thus be formulated in associative admixture with buprenorphine microparticles (as hereinbefore defined) in this way.

Furthermore, in Component (iii), particles of naloxone, or pharmaceutically-acceptable salts thereof, may also be presented upon the surfaces of, and/or between, carrier particles in compositions of the invention, but this is not essential. Such carrier particles may be water-soluble (as hereinbefore defined), or may (preferably) be water-insoluble/sparingly soluble carrier particles.

Disintegrant and/or superdisintegrant materials, may also be presented, at least in part, as particles upon the surfaces of, and/or between, carrier particles, which may or may not also carry naloxone or salt thereof. If employed in particulate form, particles of disintegrants and/or superdisintegrants may be presented with a particle size (weight and/or volume based average or mean diameter, vide supra) of between about 0.1 and about 100 μm (e.g. about 1 and about 50 μm).

Alternatively, disintegrants and/or superdisintegrants may also be present as a constituent in composite excipients. Composite excipients may be defined as co-processed excipient mixtures. Examples of composite excipients comprising superdisintegrants are Parteck® ODT, Ludipress® and Proslv® EASYtab.

Bio/mucoadhesive materials may also be presented in compositions of the invention. Such materials may be presented upon (e.g. adhered to) the surfaces of carrier particles when components of compositions of the invention are presented in the form of interactive mixtures.

Compositions of the invention may be employed in the treatment of opioid dependency and/or addiction as described hereinbefore, for example in substitution therapy programs. Opioid dependency and/or addiction may be defined in numerous ways (see, for example, www.whoint/substance_abuse/terminology/definition1), but may be characterized for example by physiological, behavioural, and cognitive phenomena wherein the use of a substance or a class of substances takes on a much higher priority for a given individual than other behaviours that once had greater value, and/or characterised by a desire (often strong, and sometimes overpowering) to take opioids and/or opiates (which may or may not have been medically prescribed). It is particularly preferred that compositions of the invention comprising naloxone are used in the treatment of opioid dependency and/or addiction.

Buprenorphine is a partial agonist at the μ-opioid receptor and an antagonist at the K-opioid receptor. It has high binding affinity at both receptors and competes with other agonists, such as methadone, heroin (diamorphine) and morphine, at the μ-opioid receptor. Opioid agonist effects of buprenorphine are less than the maximal effects of other, "full" opioid agonists, such as morphine, and are limited by a "ceiling" effect. The drug thus produces a lower degree of physical dependence than other opioid agonists, such as heroin, morphine or methadone and is therefore particularly useful in substitution therapy.

The term "pharmacologically effective amount" refers to an amount of an active ingredient, which is capable of conferring a desired therapeutic effect on a treated patient, whether administered alone or in combination with another active ingredient. Such an effect may be objective (i.e. measurable by some test or marker) or subjective (i.e. the subject gives an indication of, or feels, an effect).

Thus, appropriate pharmacologically effective amounts of buprenorphine (or salt thereof) include those that are capable of producing, and/or contributing to the production of, the desired therapeutic effect, namely decreased opioid and/or opiate craving and/or decreased illicit drug use, when administered transmucosally, whereas appropriate pharmacologically effective amounts of naloxone (or salt thereof) when employed must be sufficient so as not to compete with the above-mentioned pharmacological effect of the buprenorphine present in the composition of the invention upon transmucosal administration, but to antagonize the effect of the buprenorphine and precipitate withdrawal symptoms if an attempt is made by an opioid-addicted individual to inject a composition of the invention.

The amounts of active ingredients that may be employed in compositions of the invention may thus be determined by the skilled person, in relation to what will be most suitable for an individual patient. This is likely to vary with the route of administration, the type and severity of the condition that is to be treated, as well as the age, weight, sex, renal function, hepatic function and response of the particular patient to be treated.

The total amount of buprenorphine/salt thereof that may be employed in a composition of the invention may be in the range of about 0.1%, such as about 1%, to about 20%, such as about 10%, by weight based upon the total weight of the composition. The amount of this active ingredient may also be expressed as the amount in a unit dosage form (e.g. a tablet). In such a case, the amount of buprenorphine/salt that may be present may be sufficient to provide a dose of buprenorphine (calculated as the free base) per unit dosage form that is in the range of between about 0.1 mg, such as about 1 mg and about 50, for example about 30, such as about 20 mg (e.g. about 15 mg, e.g. about 12 mg, such as about 10 mg). Preferred ranges for the treatment of pain are about 0.1 mg to about 4 mg. Preferred ranges for substitution therapy are about 0.5 mg to about 50 mg, such as about 0.75 mg, (e.g. about 1 mg) to about 12 mg, such as about 10 mg (e.g. about 7 mg). Individual buprenorphine doses per tablet that may be mentioned include about 11.4 mg, about 8.6 mg, about 5.7 mg, about 2.9 mg and about 1.4 mg.

When employed, the total amount of naloxone/salt thereof that may be employed in a composition of the invention may be in the range about 0.125%, such as about 0.25% to about 5%, such as about 2.5%, by weight based upon the total weight of the composition. The amount of this active ingredient may also be expressed as the amount in a unit dosage form (e.g. a tablet). In such a case, the amount of naloxone/salt that may be present may be sufficient to provide a dose of naloxone (calculated as the free base) per unit dosage form that is in the range of between about 0.125 mg and about 12.5 mg, such as about 0.19 mg (e.g. about 0.25 mg) to about 3 mg, such as about 2.5 mg (e.g. about 1.75 mg).

Individual naloxone doses per tablet that may be mentioned include about 2.9 mg, about 2.2 mg, about 1.4 mg, about 0.7 mg and about 0.4 mg.

Although, for compositions of the invention containing naloxone, it is preferred that the dose ratio of buprenorphine: naloxone is maintained at about 4:1, the above-mentioned dosages are exemplary of the average case; there can, of course, be individual instances where higher or lower dosage ranges are merited, and such are within the scope of this invention.

Compositions of the invention, once prepared, are preferably directly compressed/compacted into unit dosage forms (e.g. tablets) for administration to mammalian (e.g. human) patients, for example as described hereinafter.

Compositions of the invention may be in the form of powders or, more preferably, tablets for e.g. sublingual administration. Tablets may also comprise a binder. A binder may be defined as a material that is capable of acting as a bond formation enhancer, facilitating the compression of the powder mass into coherent compacts. Suitable binders include cellulose gum and microcrystalline cellulose. If present, binder is preferably employed in an amount of between 0.5 and 20% by weight based upon the total weight of the tablet formulation. A preferred range is from 1 to 15%, such as from about 2.0 to about 12% (e.g. about 10%) by weight.

Suitable further additives and/or excipients that may be employed in compositions of the invention, in particular those in the form of tablets for e.g. sublingual administration may comprise:
  (a) lubricants (such as magnesium stearate or, preferably, sodium stearyl fumarate);
  (b) flavourings (e.g. lemon, peppermint powder or, preferably, menthol), sweeteners (e.g. neohesperidin, acesulfame K or, preferably, sucralose) and dyestuffs;
  (c) antioxidants, which may be naturally occurring or otherwise (e.g. butylated hydroxytoluene (BHT), vitamin C, vitamin E, $\beta$-carotene, uric acid, uniquion, superoxide dismutase (SOD), glutathione peroxidase or peroxidase catalase); and/or
  (d) other ingredients, such as carrier agents, preservatives and gliding agents (e.g. colloidal silica).

Compositions of the invention may be prepared by standard techniques, and using standard equipment, known to the skilled person.

When presented in the form of interactive mixtures, particles of e.g. buprenorphine/salt may be dry mixed with relevant carrier particles over a period of time that is sufficiently long to enable appropriate amounts of respective active ingredients to adhere to the surface of the carrier particles. This may also apply to other active ingredients and/or excipients defined hereinbefore.

The skilled person will appreciate that, in order to obtain a dry powder formulation in the form of an interactive mixture, larger carrier particles must be able to exert enough force to break up agglomerates of smaller particles. This ability will primarily be determined by particle density, surface roughness, shape, flowability and, particularly, relative particle sizes.

Standard mixing equipment may be used in this regard. The mixing time period is likely to vary according to the equipment used, and the skilled person will have no difficulty in determining by routine experimentation a suitable mixing time for a given combination of active ingredient and carrier particle material(s).

Interactive mixtures may also be provided using techniques other than dry mixing, which techniques will be well known to those skilled in the art.

Other ingredients may alternatively be incorporated by standard mixing or other formulation principles.

The compositions of the invention may be administered transmucosally, such as buccally, rectally, nasally or preferably sublingually by way of appropriate dosing means known to the skilled person. A sublingual tablet may be placed under the tongue, and the active ingredients absorbed through the surrounding mucous membranes.

In this respect, the compositions of the invention may be incorporated into various kinds of pharmaceutical preparations intended for transmucosal (e.g. sublingual) administration using standard techniques (see, for example, Lachman et al, "*The Theory and Practice of Industrial Pharmacy*", Lea & Febiger, $3^{rd}$ edition (1986) and "*Remington: The Science and Practice of Pharmacy*", Gennaro (ed.), Philadelphia College of Pharmacy & Sciences, 19th edition (1995)).

Pharmaceutical preparations for sublingual administration may be obtained by combining compositions of the invention with conventional pharmaceutical additives and/or excipients used in the art for such preparations, and thereafter preferably directly compressed/compacted into unit dosage forms (e.g. tablets). (See, for example, *Pharmaceutical Dosage Forms: Tablets. Volume* 1, $2^{nd}$ Edition, Lieberman et al (eds.), Marcel Dekker, New York and Basel (1989) p. 354-356 and the documents cited therein.) Suitable compacting equipment includes standard tabletting machines, such as the Kilian SP300, the Korsch EK0, the Korsch XP1, the Korsch XL100 or the Korsch PharmaPress 800.

Suitable final sublingual tablet weights are in the range of about 30 to about 400 mg, such as about 40 (e.g. about 50) to about 300 mg (e.g. about 250 mg, such as about 200 mg), for example about 50 (e.g. about 60) to 180 mg, more preferably between about 60 (e.g. about 70) and about 160 mg. Suitable final tablet diameters are in the range of about 3 to about 12 mm, for example about 4 to about 10 mm, and more preferably about 5 to about 9 mm. Suitable final tablet thicknesses are in the range of about 0.5 mm to about 4 mm, such as about 1.5 mm to about 3 mm. Various tablet shapes are possible (e.g. circular, triangular, square, diamond, polygon or oval). Suitable tablet hardnesses include crushing strengths in the range of about 10N to about 100N, for example about 15N to about 50N (depending on the size and/or weight of the tablet), according to US Pharmacopoeia method <1217>.

Irrespective of the foregoing, compositions of the invention comprising disintegrants (or other excipients that function by swelling) should be essentially free (e.g. less than about 20% by weight based on the total weight of the formulation) of water. It will be evident to the skilled person that "premature" hydration will dramatically decrease the performance of a tablet formulation in use and may result in premature dissolution of active ingredients.

Wherever the word "about" is employed herein in the context of dimensions (e.g. tablet sizes and weights, particle sizes etc.), surface coverage (e.g. of carrier particles by particles of active ingredients), amounts (e.g. relative amounts of individual constituents in a composition or a component of a composition and absolute doses (including ratios) of active ingredients), temperatures, pressures, times, pH values, concentrations, it will be appreciated that such variables are approximate and as such may vary by ±10%, for example ±5% and preferably ±2% (e.g. ±1%) from the numbers specified herein. Wherever the word "about" is employed herein in the context of pharmacokinetic properties ($C_{max}$, $t_{max}$, AUCs), etc., it will be appreciated that such variables are approximate and as such may vary by ±15%, such as ±10%.

Compositions of the invention may be administered by way of appropriate dosing means known to the skilled person. For example, a sublingual tablet may be placed under the tongue, and the active ingredients absorbed through the surrounding mucous membrane.

We have found that compositions of the invention surprisingly give rise to significantly improved bioavailability for buprenorphine when compared to prior art, commercially-available formulations. This means that formulations with lower single doses of buprenorphine may be administered by way of compositions of the invention, so reducing the "street value" of a single tablet when it comprises a composition of the invention, with more than one such tablet being required to give the same effect when illicitly administered parenterally (i.e. in "street" terms, the same "fix"). This means that compositions of the invention are less likely to be abused than prior art, commercially-available formulations (see corner et al, *Addiction*, 105, 709-718 (2010)).

Additionally, we have found that compositions of the invention comprising naloxone also surprisingly give rise to significantly (and simultaneously with buprenorphone) improved bioavailability for naloxone when compared to prior art, commercially-available formulations.

Compositions of the invention comprising naloxone thus surprisingly give rise to similar, almost parallel, degrees of improved bioavailability for both buprenorphine and naloxone, which means that the "optimal" ratio of buprenorphine to naloxone, which has been arrived at to reduce abuse potential (see, for example, Mendelson and Jones, *Drug and Alcohol Dependence*, 70, 829 (2003)), may be maintained, and doses of both active ingredients therefore lowered by an equivalent degree to preserve the same ratio.

According to a further aspect of the invention, there is provided a method of treating opioid dependency and/or addiction in a human,
  which method comprises sublingual administration to a human patient suffering from opioid dependency and/or addiction of
  at least one unit dose of a pharmaceutical composition (e.g. a tablet) comprising buprenorphine or a pharmaceutically acceptable salt thereof, in combination with naloxone or a pharmaceutically acceptable salt thereof, in about a 4:1 buprenorphine:naloxone dose ratio (calculated as free bases),
  wherein said unit dose composition comprises a dose of buprenorphine, which is about 75% of that of a random mixture compressed (RMC) tablet comprising buprenorphine, and
  which method achieves, after an initial dose in any given treatment program, a plasma-concentration time profile for buprenorphine (and/or naloxone) that is essentially equivalent to that/those exhibited by such RMC tablets.

"RMC tablets" include, but are not limited to, the commercially-available tablet product Suboxone® (NDA No. 20-733, approval date Oct. 8, 2002; buprenorphine strength 2 mg (Product No. 001; actual weight about 100 mg) and 8 mg (Product No. 002; actual weight about 400 mg)). The 8 mg tablets (at least) have a mean crushing strength (US Pharmacopeia method <1217>) of about 127 N. RMC tablet strengths are thus in the range of about 80 to about 180 N. RMC tablets are formed by compression of a random mixture, prepared by wet granulation of a standard mixture comprising buprenorphine hydrochloride, naloxone hydrochloride dihydrate, lactose monohydrate, mannitol, maize starch, povidone K30, citric acid (anhydrous granular), sodium citrate, natural lemon and lime flavour, acesulfame potassium and magnesium stearate.

By "a plasma-concentration time profile for buprenorphine and/or naloxone that is essentially equivalent to that/those exhibited by such RMC tablets", we include that, after an initial dose in any given treatment program, one or more of:
  (i) the maximum plasma concentration ($C_{max}$); and/or
  (ii) the time to maximum plasma concentration ($t_{max}$); and/or
  (iii) the total area under the plasma concentration-time curve from time zero to the time of the last measured plasma concentration ($AUC_t$); and/or
  (iv) the area under the plasma concentration-time curve from time zero to the last concentration extrapolated to infinity based on the elimination rate constant ($AUC_{inf}$),
as measured by standard pharmacokinetic monitoring means, e.g. as described in Example 2 hereinafter, for naloxone and/or, more preferably, for buprenorphine, is between about 80% and about 125% of the corresponding values obtained for the aforementioned RMC tablets.

Thus, after an initial dose in any given treatment program, for tablets comprising a dose of buprenorphine that is about 75% of a RMC tablet comprising 8 mg of buprenorphine may present:
  (i) a $C_{max}$ of between about 3.0 ng/mL and about 5.6 (such as about 4.5) ng/mL; and/or
  (ii) a $t_{max}$ that is less than about 3 hours, preferably less than about 2 hours; and/or
  (iii) an $AUC_{inf}$ that is about 25 ng·h/mL to about 40 ng·h/mL, such as about 28 ng·h/mL to about 36 ng·h/mL,
for buprenorphine; and/or
  (a) a $C_{max}$ of between about 150 pg/mL and about 300 (such as about 250) pg/mL; and/or
  (b) a $t_{max}$ that is less than about 1 hour,
for naloxone.

Thus, after an initial dose in any given treatment program, for tablets comprising a dose of buprenorphine that is about 75% of a RMC tablet comprising 8 mg of buprenorphine may present:

According to a further aspect of the invention, there is provided a method of treating opioid dependency and/or addiction in a human,
  which method comprises sublingual administration to a human patient suffering from opioid dependency and/or addiction of
  at least one unit dose of a pharmaceutical composition (e.g. a tablet) comprising buprenorphine or a pharmaceutically acceptable salt thereof, in combination with naloxone or a pharmaceutically acceptable salt thereof, in about a 4:1 buprenorphine:naloxone dose ratio (calculated as free bases),
  wherein said unit dose composition comprises a dose of buprenorphine, which is about 75% of that of a RMC tablet as hereinbefore defined, and
  which method achieves after an initial dose in any given treatment program a mean relative bioavailability compared to such RMC tablets that is:
    (A) about 1.2 to about 1.6 for buprenorphine; and/or
    (B) about 1.2 to about 2.0 for naloxone.

According to a further aspect of the invention, there is provided a method of treating opioid dependency and/or addiction in a human, which method comprises sublingual administration to a human patient suffering from opioid dependency and/or addiction of at least one unit dose of a pharmaceutical composition (e.g. a tablet) comprising buprenorphine or a pharmaceutically acceptable salt thereof, in combination with naloxone or a pharmaceutically acceptable salt thereof, wherein said tablet comprises a dose of buprenorphine or salt thereof, which is about 6 mg or about 1.5 mg, and the buprenorphine:naloxone dose ratio is about 4:1 (calculated as the free base).

Compositions of the invention may also give rise to a lower norbuprenorphine:buprenorphine ratio in plasma when compared to prior art, commercially-available formulations. A lower norbuprenorphine to buprenorphine ratio is also seen after sublingual administration of an ethanol solution compared to a tablet formulation (see Harris et al, *Clin. Pharmacokinet.*, 43, 329 (2004)) as dose is increased, suggesting that less buprenorphine is being swallowed. In addition, less norbuprenorphine is found in the plasma after parenteral administration compared to sublingual administration (Sigmon et al, *Addiction,* 101, 420 (2005)), further supporting the notion that norbuprenorphine is formed from swallowed buprenorphine by first pass metabolism through the liver. Thus, the lower norbuprenorphine:buprenorphine ratio reported herein may be reflective of the fact that more buprenorphine is absorbed over the sublingual mucosa (and so less is swallowed) than with prior art, commercially available (e.g. RMC tablet) formulations. There may also be benefits from the reduction of the norbuprenorphine:buprenorphine ratio per se, such as reduced respiratory depression (see Megarbane et al, *Toxicology and Applied Phamacology,* 212, 256 (2006)).

According to a further aspect of the invention, there is further provided a method of treating opioid dependency and/or addiction in a human, which method comprises sublingual administration of a pharmaceutical composition comprising buprenorphine or a pharmaceutically acceptable salt thereof, in combination with naloxone or a pharmaceutically acceptable salt thereof, in about a 4:1 buprenorphine:naloxone dose ratio (calculated as the free base), wherein said composition comprises a dose of buprenorphine which is about 75% of that of a RMC tablet as hereinbefore defined, to a human patient suffering from opioid dependency and/or addiction, wherein said formulation achieves after an initial dose in any given treatment program a ratio of norbuprenorphine/buprenorphine concentrations in plasma of less than about 0.8 based upon $AUC_{24}$.

Such methods may comprise administration of a composition of the invention as defined herein.

By "any given treatment program", we mean any course of treatment of a patient with a composition of the invention.

Without being limited by theory, it is understood that the compositions of the invention give rise to such surprisingly increased bioavailability when compared to prior art, commercially-available formulations, e.g. RMC tablets, such as Suboxone, because of a pH-timing effect, in which pH is lowered as hereinbefore described for a short period of time (e.g. between about 1 and about 3 minutes) after sublingual administration, resulting in improved and/or more rapid dissolution of microparticles of burprenorphine. Although such dissolution might be expected to be improved by decreasing pH, what is completely unexpected is that the degree of absorption across the sublingual mucosa does not appear to decrease. One would expect that lowering local pH would give rise to the presence of more burprenorphine in the ionized state at the site of absorption, which would in turn be expected to decrease the degree of absorption across the sublingual mucosa. The fact that the bioavailability is better per unit dose of buprenorphine for compositions of the invention than it is for prior art compositions is indeed remarkable.

According to a further aspect of the invention, there is provided a pharmaceutical composition comprising microparticles of buprenorphine or a pharmaceutically acceptable salt thereof, and particles of a weak acid or particles of weakly acidic buffer forming materials, characterized in that the composition exhibits, in an in vitro small-volume funnel dissolution method, for example as described in Example 5 hereinafter:

a) a pH drop of about 0.5 to about 5 pH units;
b) a maximum pH drop within about 1 minute of the start of the method; and
c) a return to the initial pH (±0.5) within about 3 minutes.

According to a still further aspect of the invention, there is provided a pharmaceutical composition comprising microparticles of buprenorphine or a pharmaceutically acceptable salt thereof, and particles of a weak acid or particles of weakly acidic buffer forming materials, characterized in that the composition enables the provision (at the site of administration) of a pH of between about 4.0 and about 6.5 (e.g. less than about 6.25), and the maintenance of pH within this range for an appropriate length of time (e.g. about 30 seconds, such as about 1 minute) to about 3 minutes (e.g. about 2 minutes, such as about 1.5 minutes) to facilitate dissolution of, particularly, the buprenorphine microparticles, and/or absorption of buprenorphine across the sublingual mucosa thereafter.

Compositions of the invention comprising naloxone surprisingly give rise to similar, almost parallel, degrees of improved bioavailability for both buprenorphine and naloxone, which means that the "optimal" ratio of buprenorphine to naloxone, which has been arrived at to reduce abuse potential (see, for example, Mendelson and Jones, *Drug and Alcohol Dependence,* 70, 829 (2003)), may be maintained, and doses of both active ingredients therefore lowered by an equivalent degree to preserve the same ratio.

The compositions of the invention are useful in the treatment of opioid dependency and/or addiction. Compositions of the invention may also be useful in the treatment of pain (including mild, moderate and severe pain).

According to three further aspects of the invention there are provided:

(i) a method of treatment of opioid dependency and/or addiction;
(ii) a method of treatment of pain; and
(iii) a method of treatment of both pain and opioid dependency and/or addiction, which methods comprise administration of a composition of the invention to a person suffering from, or susceptible to, the relevant conditions.

Compositions of the invention may also be administered in the induction phase (i.e. the start-up) of buprenorphine therapy, wherein buprenorphine is administered once an opioid-addicted individual has abstained from using opioids for about 12-24 hours and is in the early stages of opioid withdrawal.

According to a further aspect of the invention there is provided a method of treatment of opioid dependency and/or addiction, which method comprises administration of a composition of the invention to an individual that has abstained from using opioids for at least about 12 hours and/or is in the early stages of opioid withdrawal.

By "treatment" of pain we include the therapeutic treatment, as well as the symptomatic and palliative treatment of the condition. However, by "treatment" of opioid dependency and/or addiction, we further include the prophylaxis, or the diagnosis of the relevant condition in addition to therapeutic, symptomatic and palliative treatment. This is because, by employing buprenorphine in the treatment of pain, compositions of the invention may prevent the development of opioid dependency and/or addiction.

The compositions of the invention enable the production of unit dosage forms that are easy and inexpensive to manufacture, and which enable the rapid release and/or a rapid uptake of the active ingredients employed through the mucosa, such as the oral mucosa, thus enabling rapid relief of symptoms, such as those described hereinbefore.

The compositions of the invention also have the advantage that, if injected by an opioid addict, they do not produce the euphoric effects that such an addict seeks and indeed induce opioid withdrawal symptoms.

Compositions of the invention may also have the advantage that they may be prepared using established pharmaceutical processing methods and employ materials that are approved for use in foods or pharmaceuticals or of like regulatory status.

Compositions of the invention may also have the advantage that they may be more efficacious than, be less toxic than, be longer acting than, be more potent than, produce fewer side effects than, be more easily absorbed than, possess a better patient acceptability than, have a better pharmacokinetic profile than, and/or have other useful pharmacological, physical, or chemical properties over, pharmaceutical compositions known in the prior art, whether for use in the treatment of opioid addiction or pain or otherwise.

EXAMPLES

Figure 2:
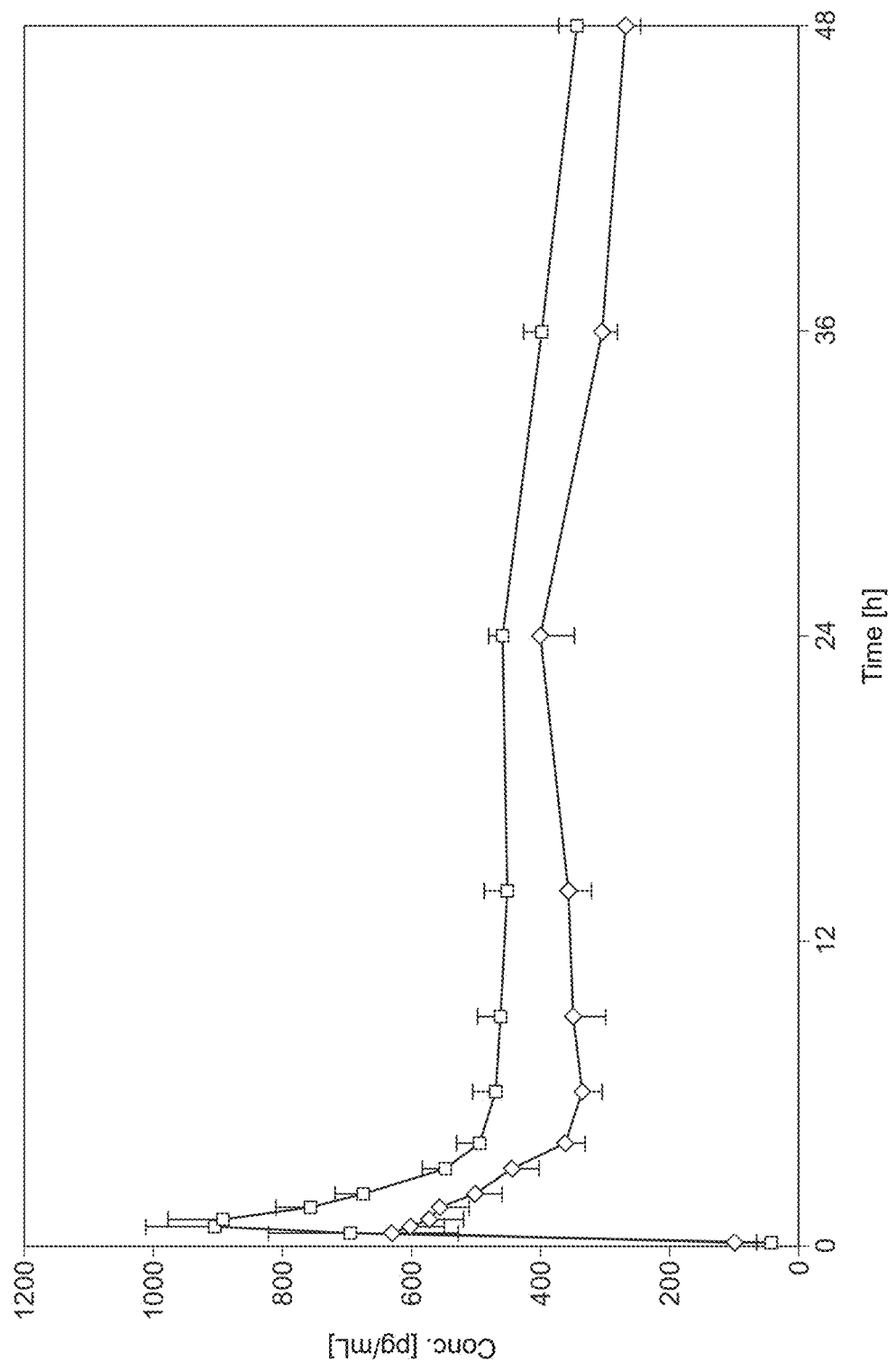
FIG. 2: Graph of plasma profile for norbuprenorphine according to Example 2.
Figure 3:
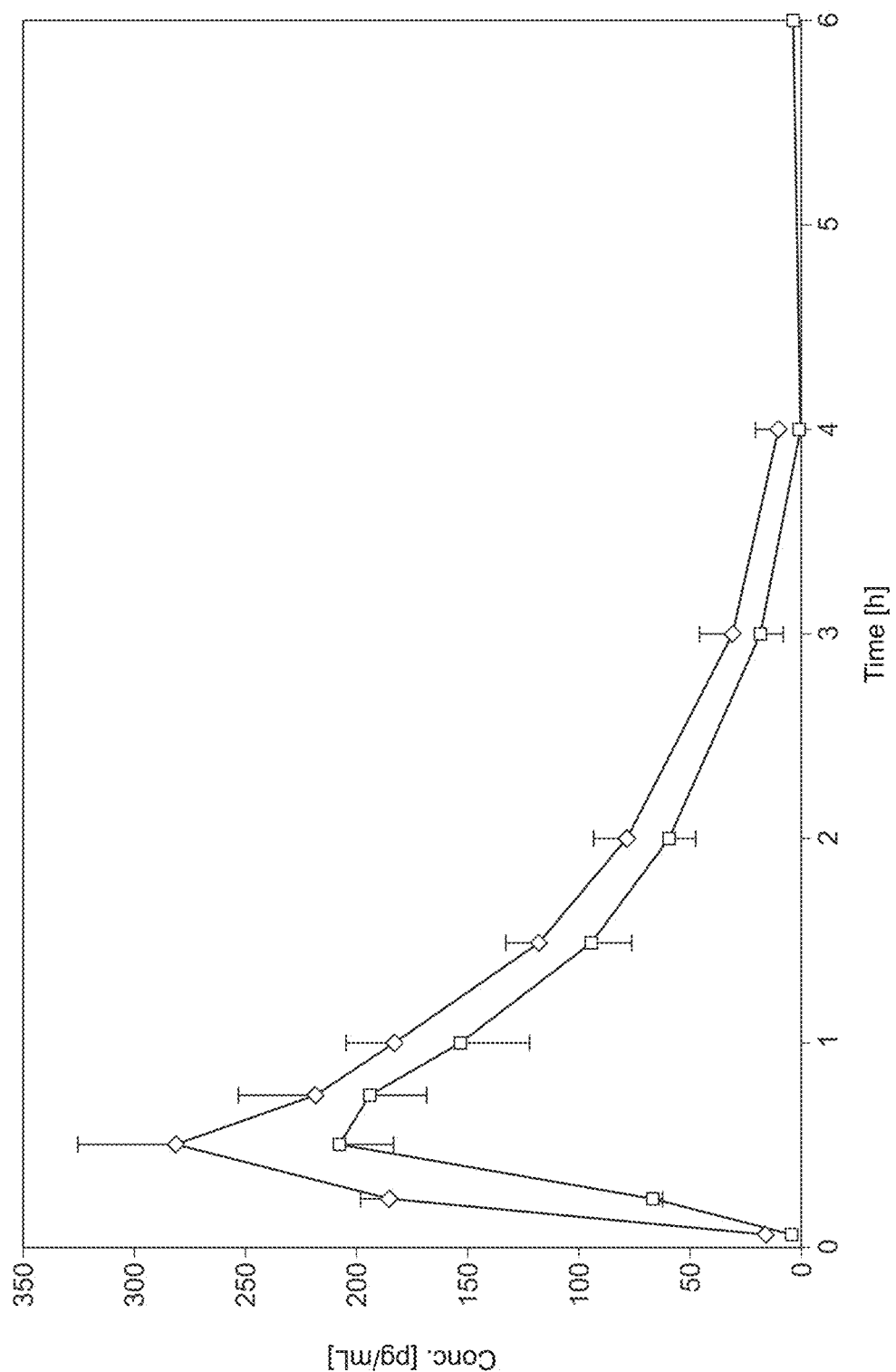
FIG. 3: Graph of plasma profile for naloxone according to Example 2.
Figure 4:
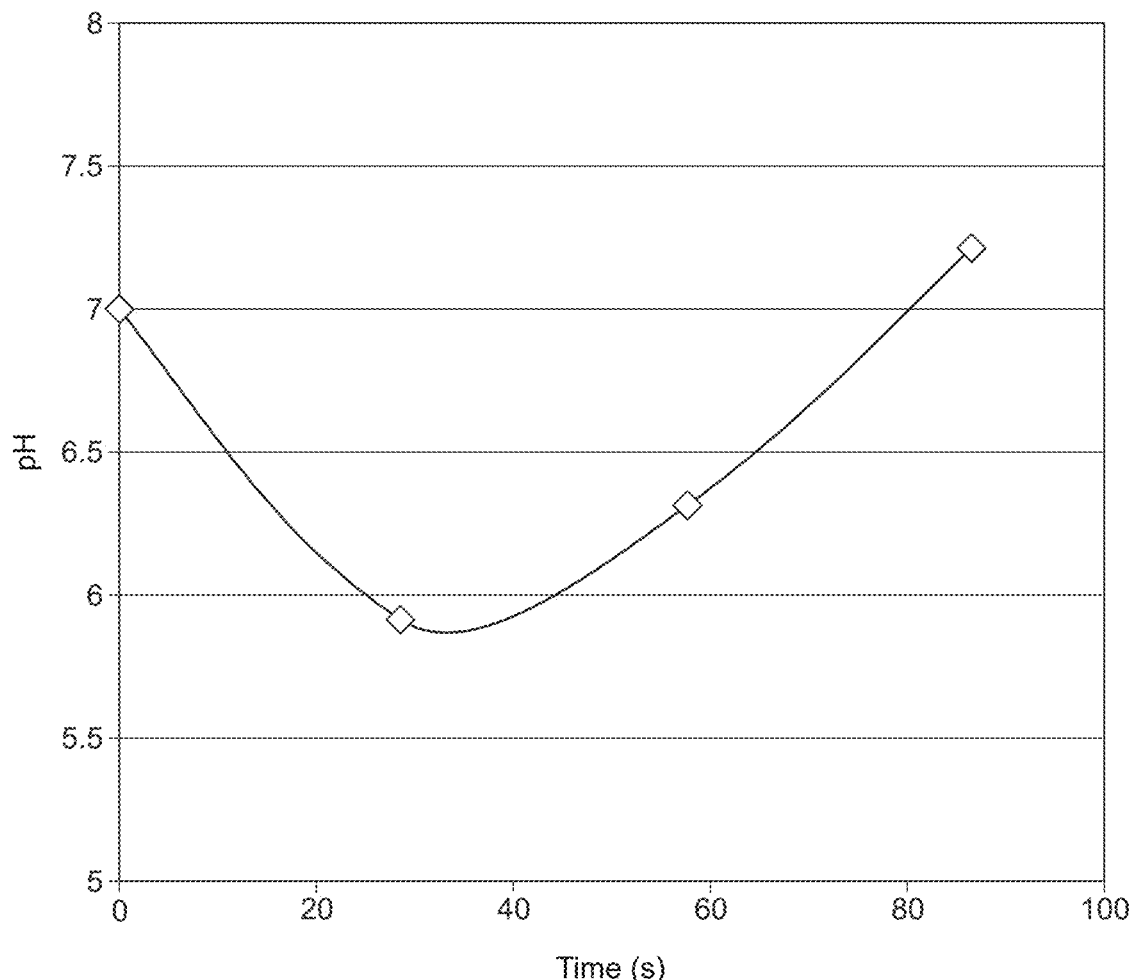
FIG. 4: Graph of pH study of placebo tablet according to Example 4.
Figure 5:
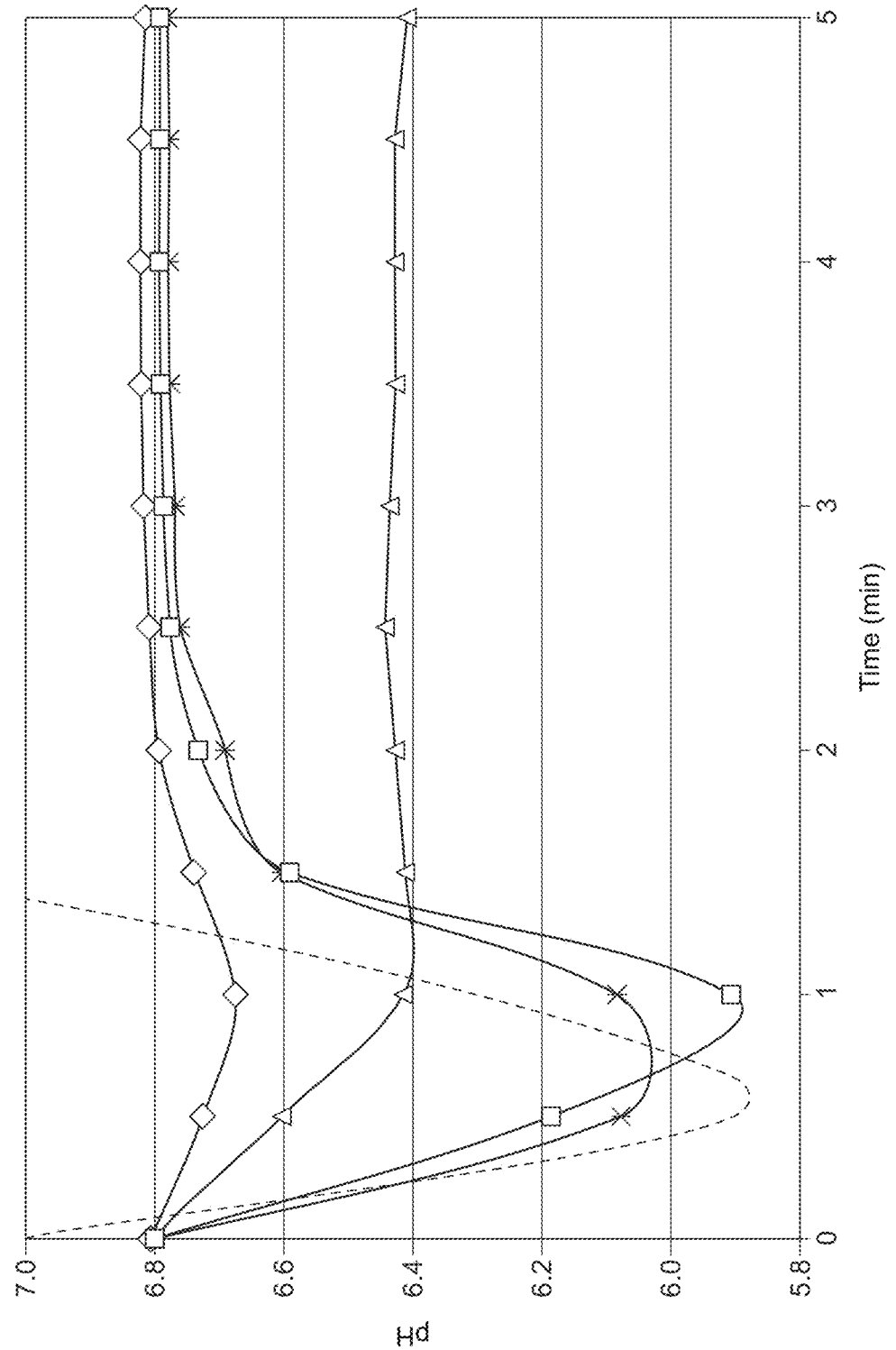
FIG. 5: Graph of in vitro pH study according to Example 5.
Figure 6:
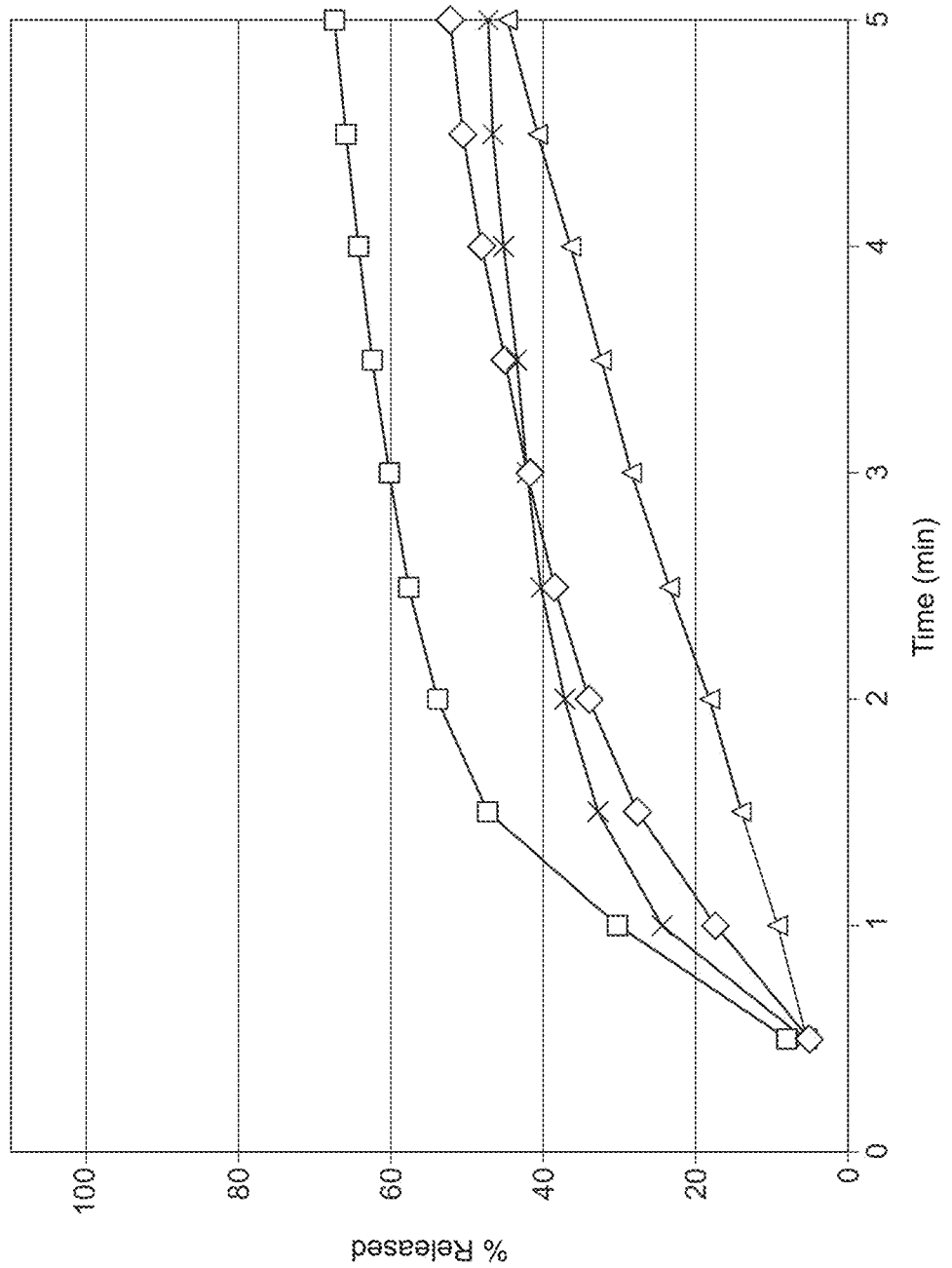
FIG. 6: Graph of release of buprenorphine according to Example 5.
Figure 7:
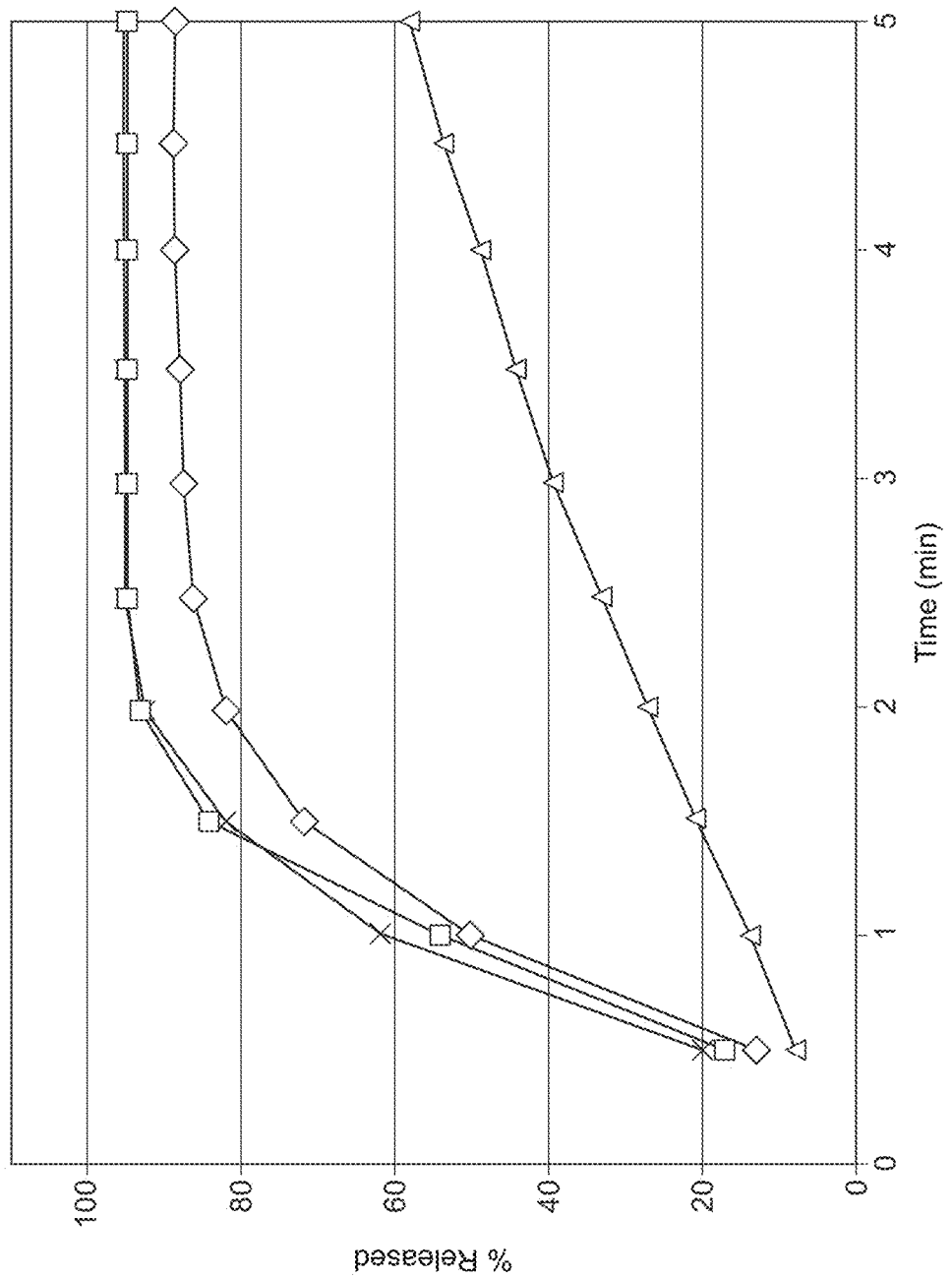
FIG. 7: Graph of release of naloxone according to Example 5.
Figure 8:
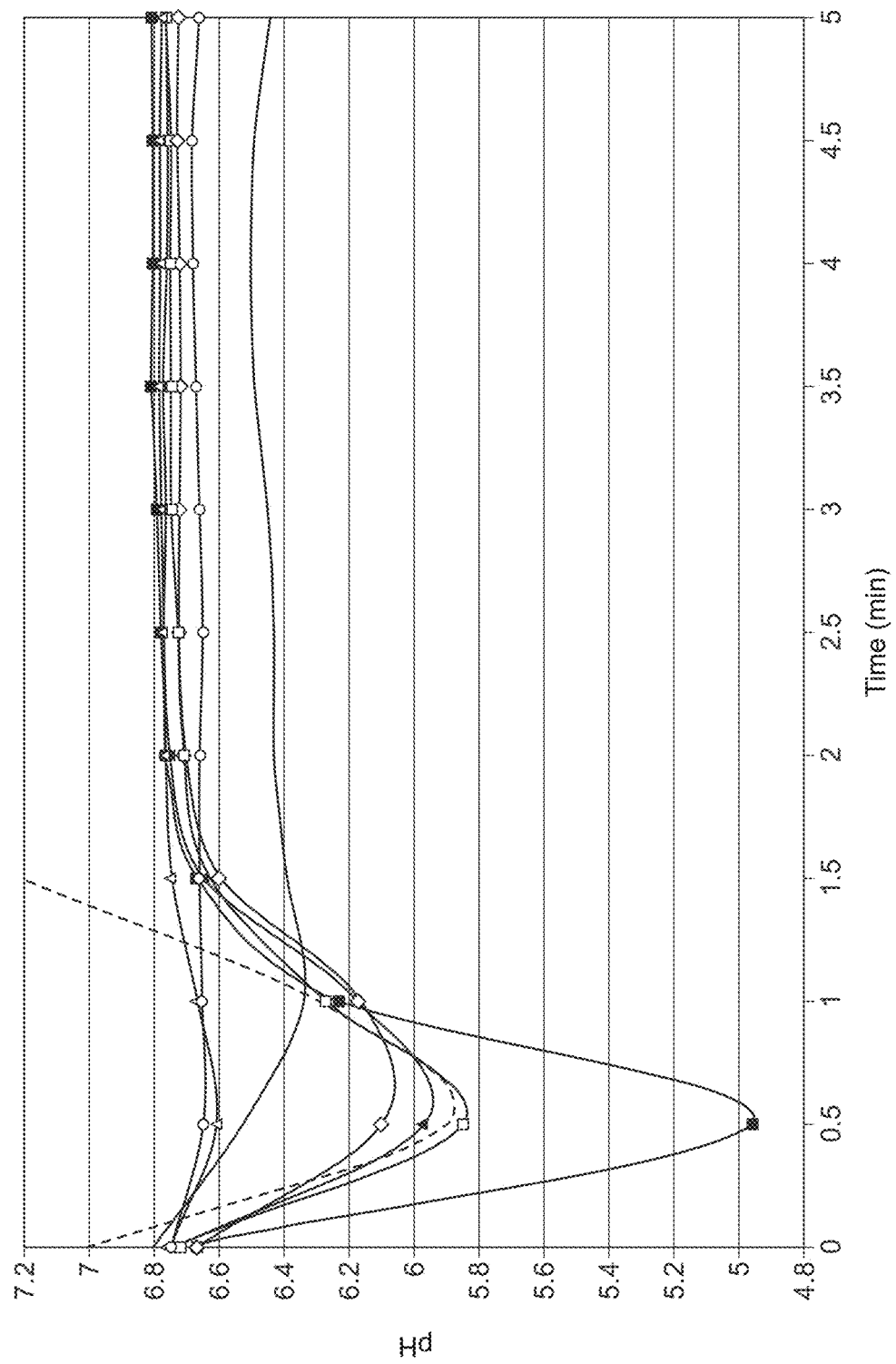
FIG. 8: Graph of in vitro pH study of several formulations according to Example 9.
Figure 9:
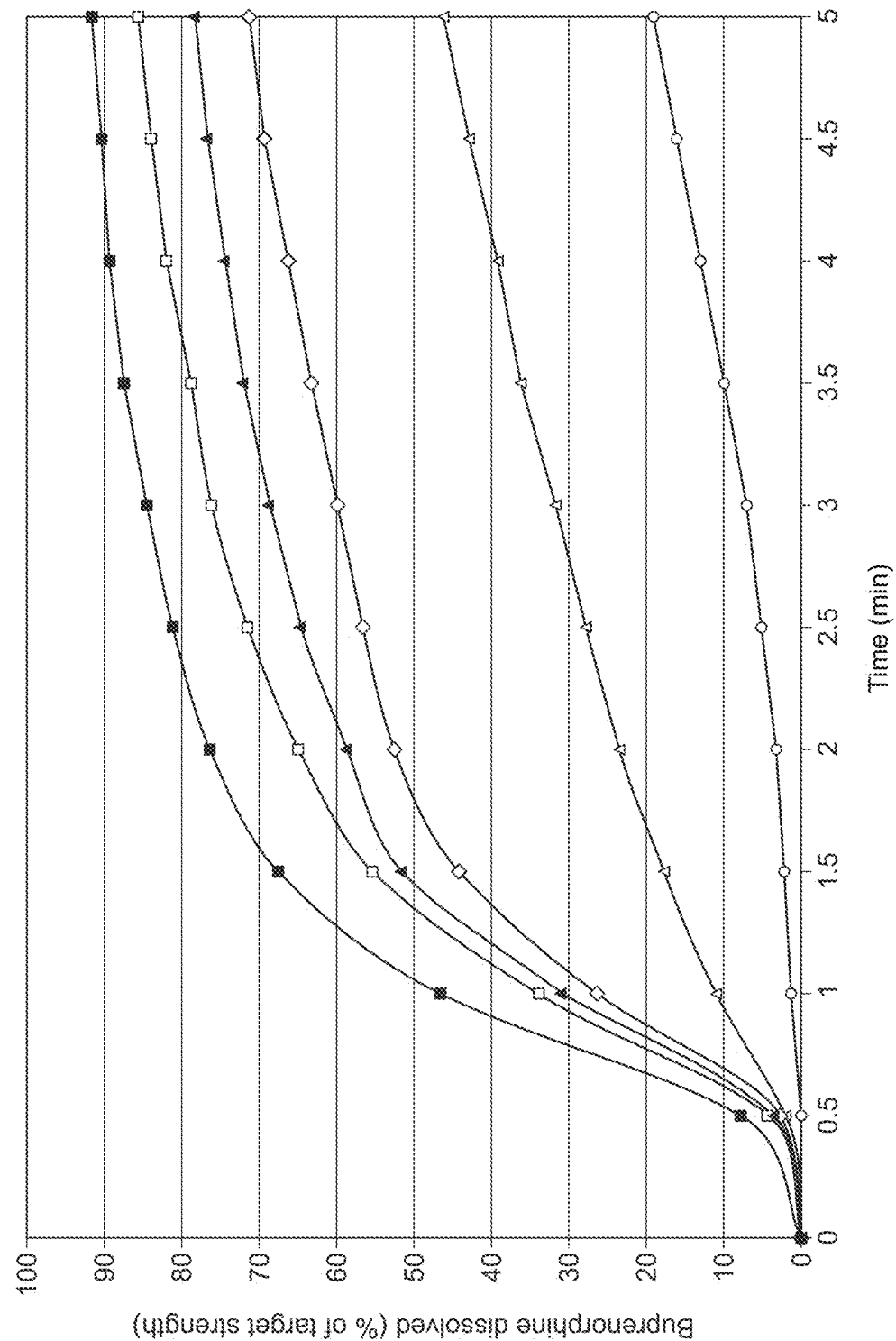
FIG. 9: Graph of release of buprenorphine according to Example 9.

The invention is illustrated by way of the following examples, with reference to the attached figures in which analyte concentration-time plasma profiles are presented in linear scale plots for buprenorphine (FIG. 1), norbuprenorphine (FIG. 2) and naloxone (FIG. 3) following sublingual administration of tablets comprising a composition of the invention (diamonds) and the commercially-available comparator, Suboxone® (squares); FIG. 4 shows an in vivo sublingual pH profile obtained for a placebo composition (analogous to one prepared in accordance with the invention); FIG. 5 shows comparative in vitro pH profiles for composition of the invention versus Suboxone and other comparators in a small-volume funnel dissolution test; FIGS. 6 and 7 show release of buprenorphine and naloxone, respectively, from the compositions referred to in FIG. 5; FIG. 8 shows comparative in vitro pH profiles for compositions of the invention versus Suboxone and other comparators in a small-volume funnel dissolution test; and FIG. 9 show release of buprenorphine from compositions referred to in FIG. 8.

Example 1

Buprenorphine/Naloxone Sublingual Tablets I

Naloxone hydrochloride dihydrate (Macfarlan Smith, Edinburgh, UK) and buprenorphine hydrochloride (Macfarlan Smith, Edinburgh, UK) were micronised using an air jet mill (Pilotmill-1/Food and Pharma Systems, Italy). The volume based mean particle size (diameter) of the buprenorphine was 3.4 μm and of the naloxone was 4.6 μm.

9.15 g of the micronised naloxone hydrochloride dihydrate was mixed together with microcrystalline cellulose (47.50 g; Avicel™ PH102 (mean particle size 100 μm), FMC Biopolymer, Cork, Ireland) and croscarmellose sodium (18.00 g; AcDiSol™, FMC Biopolymer) in a tumble blender (Turbula, WAG, Switzerland) for 40 hours.

32.40 g of the micronised buprenorphine hydrochloride was mixed together with mannitol (314.20 g; Pearlitol™ 200SD, Roquette, Lestrem, France), sieved citric acid (15.00 g; fine granular 16/40 grade, DSM, Switzerland, Basel) and sieved (to avoid agglomeration) sodium citrate (48.75 g) Emprove™ cryst., Merck, Darmstadt, Germany) in a tumble blender for 40 hours.

Menthol (5.00 g; Emprove™ cryst., Merck) was mortared until a fine powder was formed. This and also acesulfame potassium (5.00 g; Sunett Pharma D, Nutrinova, Kelsterbach, Germany) and anhydrous colloidal silica (5.00 g; Aerosil™ 200 Pharma, Evonik Degussa, Hanau-Wolfgang, Germany) were added by sieving into the buprenorphine premix, together with the naloxone premix, and the whole mixed together in a tumble blender for 1 hour.

Sodium stearyl fumarate (10.00 g; Pruv™, JRS Pharma, Polanco, Spain) was then added by sieving into this mixture and mixing continued in the tumble blender for 5 minutes.

The final powder mixture was then compressed into tablets in a tablet machine (Korsch XP1) equipped with 7 mm round, flat faced, radius-edged punches, to a tablet weight of 102 mg and a tablet crushing strength of 35 N.

Example 2

Clinical Trial

The tablets of Example 1 were sublingually administered in an open-label, 2-period crossover study with randomised treatment sequence.

The study comprised a screening visit conducted within 28 days prior to first treatment, two treatment periods each of 4 days length (Day −1 to Day 3) and a washout period of at least 10 days between treatment periods. During the treatment periods, subjects were admitted to the clinical unit on the morning prior to first dosing (Day −1) and remained in the unit until the completion of Day 3 procedures. A follow-up visit was carried out 5 to 10 days after completion of the second Investigational Medicinal Product (IMP) administration.

The IMPs were sublingual tablet prepared in accordance with Example 1 (6 mg buprenorphine/1.5 mg naloxone; hereafter "formulation of the invention") and, as the reference product, Suboxone sublingual tablet (8 mg buprenorphine/2 mg naloxone; Reckitt Benckiser Healthcare Ltd, Hull, UK). Treatment with formulation of the invention, or Suboxone (1 tablet) in alternate periods was open-label and was administered on Day 1 in each treatment period.

Naltrexone tablets (Nalorex®, 50 mg, Bristol-Myers Squibb Pharmaceuticals Ltd; Uxbridge, UK) were administered orally (one 50 mg tablet), at −24 to −16 hours, −1 hour (±5 minutes) and +24 hours (±1 hour) in relation to administration of IMP, as a naltrexone block in the study (in order to alleviate opioid side effects during the study).

Eighteen healthy male volunteers aged between 18 and 50 years were enrolled. These received both treatments and were evaluated. The mean age was 29.8 years and ages ranged from 19 to 49 years. All subjects were male Caucasians. The mean weight was 78.16 kg and ranged from 63.0 to 93.5 kg. The mean body mass index of the subjects was 25.05 kg/m$^2$ and ranged from 20.7 to 28.9 kg/m$^2$.

All subjects (except one) reported current alcohol use ranging from 1 to 20 units per week. No subject was a current smoker. All subjects reported current caffeine use of 1 to 5 cups or cans per day. No subject had been treated with opioids within 1 year prior to screening.

No subject reported any pre-study medication (taken within 2 weeks prior to screening). One subject reported ongoing use of antihistamines for systemic use by oral tablet or capsule to treat seasonal allergic rhinitis.

Trial medication was administered in the clinic under the supervision of clinic personnel.

All subjects who were enrolled in the study and who received at least one dose of trial medication. All randomised subjects who received at least one treatment, had at least one evaluable plasma profile and had no major protocol deviations that could have a substantial effect on the buprenorphine, norbuprenorphine or naloxone plasma concentration profile, such as:

swallowing of study medication (applies to both formulation of the invention and Suboxone)
  vomiting within 4 hours after administration of either type of tablet
  having a pre-dose quantifiable concentration that is >5% of a subject's $C_{max}$ All randomised subjects who received at least one treatment and had disintegration or acceptability data present for at least one treatment.

Pharmacokinetic (PK) variables were based on plasma concentrations of buprenorphine, norbuprenorphine (a metabolite of buprenorphine) and naloxone and were calculated using standard, non-compartmental methods. The PK non-compartmental analysis was performed using WinNonlin™ Professional version 5.2. Data permitting, the following parameters were determined:

$t_{lag}$ lag time before the start of absorption
  $C_{max}$ maximum plasma concentration
  $t_{max}$ time to reach maximum plasma concentration
  $AUC_{0-t}$ area under the plasma concentration-time curve from time zero to the time of the last quantifiable plasma concentration
  $AUC_{0-48}$ area under the plasma concentration-time curve from time zero to 48 hours post-dose
  MR metabolic ratio In addition, the relative bioavailability ($F_{rel}$) of formulation of the invention to Suboxone was derived based on dose-adjusted PK data.

Subjects were classified as evaluable or non-evaluable with respect to the PK evaluation by the pharmacokineticist after examining the subjects PK profiles and taking into account any deviations with respect to those listed above. The PK analyses based on the PK population included only those subjects with evaluable PK data.

Actual blood sampling times for buprenorphine, norbuprenorphine and naloxone were converted to a time from dosing (elapsed time). Elapsed times were listed by subject for each treatment, together with the individual buprenorphine, norbuprenorphine and naloxone concentrations. Elapsed times were used in the PK analysis.

The buprenorphine, norbuprenorphine and naloxone concentrations were summarised by descriptive statistics of number of missing samples, number of samples less than the lower limit of quantification (<LOQ), n, arithmetic mean, SD, CV (%), geometric mean, 95% confidence intervals (CI) for the arithmetic mean, median, minimum and maximum. All buprenorphine, norbuprenorphine and naloxone concentrations <LOQ were set to zero for the purpose of calculating descriptive statistics. If at any time-point ⅓ or more of subjects had values <LOQ, descriptive statistics were not calculated.

The PK parameters $C_{max}$, $AUC_{0-t}$ and $AUC_{0-48}$ of buprenorphine, norbuprenorphine and naloxone were compared between treatments using a mixed effects Analysis of Variance (ANOVA) procedure.

Arithmetic mean (+SEM) analyte concentration-time plasma profiles are presented in linear scale plots for each analyte in FIGS. 1 (buprenorphine), 2 (norbuprenorphine) and 3 (naloxone) with both treatments included on each plot. It can be seen from these figures that, for both buprenorphine and norbuprenorphine after administration of formulation of the invention (diamonds), and Suboxone (squares), plasma concentrations of all three analytes increased to a maximum then declined in a biphasic manner.

In relation to other PK parameters:

(i) on average, the lag time was slightly shorter after treatment with formulation of the invention compared to Suboxone by 15% for buprenorphine, 29% for norbuprenorphine and 34% for naloxone;

(ii) the range of times at which maximal concentrations were attained ($t_{max}$) was similar between treatments for all analytes. Median $t_{max}$ values were less than or equal to 1 h for buprenorphine and naloxone indicating rapid sublingual absorption following administration of both formulation of the invention and Suboxone. For norbuprenorphine, $t_{max}$ was generally similar to buprenorphine after both treatments indicating metabolism of buprenorphine to norbuprenorphine was rapid;

(iii) the mean metabolite ratios exceeded 0.5 indicating extensive metabolic conversion of buprenorphine to norbuprenorphine, with conversion being 31% lower following administration of formulation of the invention compared to Suboxone. This result is significant as it means that more buprenorphine is absorbed sublingually in the case of formulation of the invention;

(iv) the doses of both buprenorphine and naloxone were lower in the formulation of the invention, but mean systemic exposure, in terms of $C_{max}$ and AUC, of buprenorphine and naloxone were higher when compared to Suboxone, and, as stated above, the values were lower for norbuprenorphine; and (v) the mean relative bioavailabilities of formulation of the invention to Suboxone were 1.659 and 2.056 for buprenorphine and naloxone respectively, indicating higher dose-normalised systemic exposure following administration of formulation of the invention. For norbuprenorphine the dose-normalised systemic exposure appeared to be similar between treatments with a mean relative bioavailability of 1.084. The buprenorphine result is surprising. The reported relative bioavailability of a sublingually-administered ethanol solution comprising buprenorphine (where conditions are theoretically optimised for rapid absorption over the sublingual mucosa) compared to Suboxone was reported to be 1.5 (see Compton et al, *Drug and Alcohol Dependence,* 82, 25 (2006)). The fact that the relative number reported in this study for a solid sublingual tablet was even higher than that reported for a solution is remarkable.

Disintegration time of the tablets was assessed by either a nurse or a physician by mouth inspections, and was also reported by the subjects, who were given thorough instructions of the dosing procedures prior to dosing on Day 1 in both treatment periods, including the procedures for observer and subject assessments of disintegration. Subjects were to report any premature swallowing.

The sublingual space and the tablet were examined to determine the time to disintegration. The tablet residues were characterised as 'intact', 'fragments', 'paste like residue' or 'dissolved'. Inspections were carried out every 2 minutes and the findings recorded until the tablet was completely disintegrated. In addition, the subject was instructed to indicate when they thought the IMP was dissolved by raising their hand or to indicate whether they had swallowed the tablet before it was dissolved. The time of dissolution or swallowing was recorded.

Median time to non-intact tablets was 2 minutes for the formulation of the invention and was 8 minutes for Suboxone.

Summary and Conclusions

The above-reported parameter ratios suggest that the formulation of the invention resulted in slightly higher plasma buprenorphine and naloxone concentrations and slightly lower plasma norbuprenorphine concentrations than the comparator. The former result is despite the initial dose being lower which indicates that it may be possible to reduce dose still further. Tablets comprising formulations of the invention also disintegrated faster than the comparator.

Example 3

Buprenorphine/Naloxone Sublingual Tablets II 3.97 g of micronized naloxone hydrochloride dihydrate was mixed together with microcrystalline cellulose (20.00 g; Avicel™ PH102 (mean particle size 100 μm), FMC Biopolymer) and croscarmellose sodium (7.20 g; AcDiSol™, FMC Biopolymer) in a tumble blender (Turbula, WAG, Switzerland) for 40 hours.

14.04 g of micronised buprenorphine hydrochloride was mixed together with mannitol (130.30 g; Pearlitol™ 200SD, Roquette, Lestrem, France), sieved citric acid (6.00 g; fine granular 16/40 grade, DSM, Switzerland, Basel) and sieved (to avoid agglomeration), sodium citrate (19.50 g) Emprove™ cryst., Merck, Darmstadt, Germany) and blended in a tumble blender for 42 hours.

Menthol (2.00 g; Emprove™ cryst., Merck KGaA, Darmstadt, Germany) was mortared until a fine powder was formed and was blended with silicon dioxide, colloidal (0.20 g; Aerosil™ 200 Pharma), (1:1 volume ratio).

Sucralose (6.00 g, Merck KGaA, Darmstadt, Germany) was added to the buprenorphine premix. The naloxone premix and the rest of the silicon dioxide colloidal (2.80 g) were added by co-sieving into the buprenorphine premix. The menthol-silicon dioxide blend was added by sieving to the buprenorphine premix and all ingredients were mixed for 1 hour.

Sodium stearyl fumarate (8.00 g; Pruv™, JRS Pharma, Polanco, Spain) was then added by sieving into this mixture and mixing continued in the tumble blender for 10 minutes.

The final powder mixture was then compressed into tablets in a tablet machine (Korsch EK0) equipped with 7 mm round, flat faced, radius-edged to punches, to a tablet weight of 110 mg and a tablet crushing strength of 30-35 N.

Example 4

In Vivo Experiment

Placebo tablets prepared according to the procedure described in Example 1 above (excluding buprenorpine, but including naloxone) were first administered sublingually.

Sublingual saliva pH was measured in vivo using a Schott CG 842P pH Meter attached to a Schott Flatrode™-electrode (pH 0-14, 0-60° C.). The Flatrode™ has a super-flat membrane for surface measurements and a robust plastic shaft with a ring diaphragm, which guarantees a quick response via enhanced contact between the sample and reference. The diameter of the flat surface of the electrode is 6.0 mm giving a measuring surface of 0.28 $cm^2$.

The Flatrode was positioned (at an open mouth angle of 45°) gently behind the lower teeth, just beside the tablet in the mouth. A very gentle pressure was applied in order to measure pH in saliva rather than venous blood pH (typically pH 7.4).

pH was measured at time intervals of 0, 30, 60 and 90 seconds (over 5 seconds until a stable value was observed). Care was taken to avoid accidental withdrawal of dissolved powder by the electrode. The mouth was shut between measurements with no active swallowing.

Triplicate runs were carried out to ensure a reliable pH-profile. Between runs, the mouth was washed thoroughly with water and pH measured prior to administration to obtain a new zero-value.

The results indicated that the pH decrease peaked at around 35-40 seconds. It can be seen from FIG. 4 that the body rapidly compensates for the modified pH and also slightly overcompensates, and that the window of opportunity (i.e. the time range with a 0.5 pH unit decrease (at least) compared to resting pH) for increased solubility of buprenorphine is only about 80 seconds, starting after 10 seconds (n=4).

Example 5

Comparative In Vitro Small-Volume Funnel Dissolution Experiment I

In addition to the sublingual tablets described in Example 3 above, two other otherwise identical batches of sublingual tablets were prepared using the same methodology, except that, in one case, the buprenorphine hydrochloride was not micronized, and in the other, no citric acid and sodium citrate were included (instead a further 12.75 mg per tablet of mannitol was included.

Tablets form the three above-mentioned tablet batches, as well as Suboxone tablets (buprenorphine 8 mg/naloxone 2 mg; Reckitt Benckiser Healthcare Ltd, Hull, UK) were placed on top of a Porosity 1 20 mm diameter silica filter in a 55 mm (upper inner diameter) glass funnel.

Potassium phosphate buffer with a pH of 6.8 (USP/NF), which mimics saliva, was allowed to drip through a soft PVC plastic tube with an inner diameter of 3 mm onto the tablets at a rate, set by a peristaltic pump (Flocon 1003), of 2 mL per minute. The distance between the end of the plastic tube and the silica filter in the funnel was set at approximately 7.5 cm, in order, along with the dripping rate, to correspond to a force similar to the pressure of the underside of the tongue. The small amounts of water involved endeavour to mimic the low amounts of water available in vivo under the human tongue.

pH was measured over time using a Mettler Toledo InLab Expert Pro electrode (pH 0-14; 0-100° C.) attached to standard Mettler Toledo 340 pH meter positioned at the outlet of the glass funnel.

To measure the release of active pharmaceutical ingredients over time from the tablets, a glass beaker equipped with a magnetic stirrer containing 490 mL of potassium phosphate buffer pH 6.8 (USP/NF) collected the drops from the funnel.

800 μL samples were withdrawn from the beaker using a calibrated micropipette at intervals of 0.5, 1.0, 1.5, 2.0, 2.5, 3.0, 3.5, 4.0, 4.5, 5.0, 10.0, 15.0 and 20.0 minutes. These samples were emptied into 1 mL vials already containing 200 µL of diluted phosphoric acid. No additional buffer was added to the collection beaker to compensate. It started with a volume of 490 mL and ended with a volume of 520 mL (the difference between 40 mL added to the beaker over 20 minutes, and 10.4 mL removed in total (13×0.8 mL) is 29.6 mL (i.e. about 30 mL)). It was decided to start at 490 mL instead of 485 mL to be as close to 500 mL for as long a period as possible. The exact individual volumes were of course calculated for each sample.

Three tablets from each of the four tablet table batches in the trial were analysed as release test samples. Amounts of buprenorphine and naloxone were measured using HPLC (Agilent 1000; Diode array-detector, gradient pump, autosampler, column oven), with a gradient method with UV detection at 210 nm.

pH was plotted over time for the following four tablet batches and the results are shown in FIG. 5 (tablets prepared according to Example 3 (squares); non-micronised buprenorphine equivalents (crosses); equivalents without citric acid/sodium citrate (diamonds); and Suboxone (triangles)). The dashed line in FIG. 5 is the superimposed in vivo profile from FIG. 4.

The drug release profiles over the first 5 minutes for buprenorphine and naloxone are presented in FIGS. 6, and 7, respectively. Although Suboxone has a 23% higher drug loading than all of the other tablets, it produces a buprenorphine release after 20 minutes through the funnel of only 75% of that of the tablets according to the invention. The difference is most noticeable over the first 5 minutes.

Example 6

Buprenorphine/Naloxone Sublingual Tablets III 336.0 g of micronized naloxone hydrochloride dihydrate was mixed together with microcrystalline cellulose (2000.0 g; Avicel™ PH102 (mean particle size 100 µm), FMC Biopolymer, Wallington, Little Island, Co. Cork, Ireland) and croscarmellose sodium (720.0 g; AcDiSol™, FMC Biopolymer, Wallington, Little Island, Co. Cork, Ireland) in a 12 L double cone blender (Sewin, Zickert systems, Kungsbacka, Sweden) for 3 hours.

Citric acid (600.0 g; fine granular 16/40 grade, DSM, Switzerland, Basel), sodium citrate (1950.0 g Emprove™ cryst., Merck, Darmstadt, Germany) and silicon dioxide, colloidal (480.0 g Aerosil™ 200 Pharma, Evonik Degussa GmbH, Rheinfelden, Germany) were deagglomerated together with Quadro comil apparatus (Quadro Engineering, Ontario, Canada) and premixed with two thirds of a premeasured amount of mannitol (8737.3 g; Pearlitol™ 200SD, Roquette, Lestrem, France) in a 60 L double cone blender (Sewin, Zickert systems, Kungsbacka, Sweden) for 5 minutes.

1188.0 g of the micronised buprenorphine hydrochloride was added to the premix and the other third of the mannitol (4368.7 g) was added on top of the buprenorphine hydrochloride and all ingredients were mixed for 3 hours.

Menthol (200.0 g; Emprove™ cryst., Merck KGaA, Darmstadt, Germany) was milled with Quadro comill. Silicon dioxide, colloidal (20.0 g) and milled menthol (1:1 volume ratio) was processed with Quadro comill in order to deagglomerate the silicon dioxide (colloidal).

Sucralose (600.0 g, Merck KGaA, Darmstadt, Germany), the naloxone premix and the menthol-silicon dioxide blend were added to the buprenorphine premix and all ingredients were mixed for 1 hour.

Sodium stearyl fumarate (800.0 g; Pruv™, JRS Pharma, Polanco, Spain) was deagglomerated with Quadro comil and added to double cone blender and mixed for 10 minutes.

The final powder mixture was then compressed into tablets in a tablet machine (Korsch XL100, Korsch AG, Berlin, Germany) equipped with 7 mm round, flat faced, radius-edged punches, to a tablet weight of 110 mg and a tablet crushing strength of 30-35 N.

Example 7

Buprenorphine/Naloxone Sublingual Tablets IV 200,000 100 mg buprenorphine/naloxone (4:1 dose ratio) tablets comprising a 1.4 mg dose of buprenorphine (calculated as the free base) were prepared using essentially the same procedure as described in Example 6.

Example 8

Buprenorphine/Naloxone Sublingual Tablets V 200,000 110 mg buprenorphine/naloxone (4:1 dose ratio) tablets comprising a 5.7 mg dose of buprenorphine (calculated as the free base) were prepared using essentially the same procedure as described in Example 6.

Example 9

Comparative In Vitro Small-Volume Funnel Dissolution Experiment II

Using the in vitro small-volume funnel dissolution procedure described in Example 5, pH profiles (measurement of pH over time) were obtained for:
  (a) buprenorphine/naloxone sublingual tablets prepared as described in Example 8;
  (b) buprenorphine/naloxone sublingual tablets prepared essentially as described in Example 8, except that the citric acid and sodium citrate were included during the mixing step in which the two APIs are mixed together;
  (c) buprenorphine/naloxone sublingual tablets prepared essentially as described in Example 8, but without citric acid (i.e. sodium citrate only);
  (d) buprenorphine/naloxone sublingual tablets prepared essentially as described in Example 8, but without sodium citrate (i.e. citric acid only);
  (e) buprenorphine/naloxone sublingual tablets prepared essentially as described in Example 8, except that tartaric acid (Sigma-Aldrich) was used instead of citric acid and sodium citrate; and
  (f) Suboxone® film (8 mg buprenorphine/2 mg naloxone; Reckitt Benckiser Healthcare Ltd, Hull, UK).

In the case of tablets (c), and (d), an equivalent amount of mannitol was employed instead of the citric acid, and the sodium citrate, respectively, that was excluded. In the case of tablets (e), 2 mg (per tablet) of tartaric acid and an extra 10.75 mg (per tablet) of mannitol were employed.

The results are shown in FIG. 8 (tablets (a)—diamonds; tablets (b)—black triangles; tablets (c)—white triangles; tablets (d)—black squares; tablets (e)—white squares; and Suboxone films (f)—circles). Also superimposed on FIG. 8 are:
  (i) the in vivo profile from FIG. 4 (dashed line); and
  (ii) the in vitro pH profile previously obtained for Suboxone® tablets (solid line; originally presented in FIG. 5).

The drug release/dissolution profiles over the first 5 minutes for buprenorphine are presented in FIG. 9. It can be clearly seen from FIGS. 8 and 9 taken together that drug dissolution correlates strongly with how much the pH is lowered during first 1 minute to 2 minutes after the start of the experiment (corresponding to sublingual administration in vivo). It can also be seen that the largest pH drop, and the highest dissolution rate, were obtained when citric acid alone was used.

The invention claimed is:

1. A pharmaceutical composition in the form of a compressed tablet suitable for sublingual administration, which comprises:
   (i) buprenorphine or a pharmaceutically-acceptable salt thereof provided in the form of microparticles in a dosage amount (calculated as the free base) that is 11.4 mg (±2%), 8.6 mg (±2%), or 5.7 mg (±2%);
   (ii) naloxone or a pharmaceutically-acceptable salt thereof provided in the form of particles in an amount (calculated as the free base) that is about ¼ of the above doses of buprenorphine or salt thereof;
   (iii) particles comprising a weak acid; and
   (iv) a disintegrant,
   wherein the tablet weighs no more than about 250 mg and has a hardness that is in the range of about 10N to about 100N, as measured by the US Pharmacopoeia method <1217>.

2. The composition as claimed in claim 1, wherein the disintegrant is selected from the group croscarmellose sodium, sodium starch glycolate, crosslinked polyvinylpyrrolidone, and mixtures thereof.

3. The composition as claimed in claim 1, wherein the weak acid is citric acid.

4. The composition as claimed in claim 1, wherein the tablet further comprises a binder, carrier particles, particles comprising sodium citrate or any combination of these.

5. The composition as claimed in claim 4, wherein the weak acid is citric acid, and the particles comprising citric acid and the particles comprising sodium citrate are separate particles.

6. The composition as claimed in claim 1, wherein the tablet has a hardness that is in the range of about 15N to about 50N.

7. A method of treatment of a patient for opioid dependency and/or addiction, or for pain, which method comprises administering to said patient a pharmaceutical composition according to claim 1.

8. A pharmaceutical composition in the form of a compressed tablet suitable for sublingual administration, which comprises:
   (i) buprenorphine or a pharmaceutically-acceptable salt thereof provided in the form of microparticles in a dosage amount (calculated as the free base) that is 2.9 mg (±2%);
   (ii) naloxone or a pharmaceutically-acceptable salt thereof provided in the form of particles in a dosage amount (calculated as the free base) that is about ¼ of the above dose of buprenorphine or salt thereof;
   (iii) particles comprising a weak acid; and
   (iv) a disintegrant,
   wherein the tablet weighs no more than about 100 mg and has a hardness that is in the range of about 10N to about 100N, as measured by the US Pharmacopoeia method <1217>.

9. The composition as claimed in claim 8, wherein the disintegrant is selected from the group croscarmellose sodium, sodium starch glycolate, crosslinked polyvinylpyrrolidone, and mixtures thereof.

10. The composition as claimed in claim 8, wherein the weak acid is citric acid.

11. The composition as claimed in claim 8, wherein the tablet further comprises a binder, carrier particles, particles comprising sodium citrate or any combination of these.

12. The composition as claimed in claim 11, wherein the weak acid is citric acid, and the particles comprising citric acid and the particles comprising sodium citrate are separate particles.

13. The composition as claimed in claim 8, wherein the tablet has a hardness that is in the range of about 15N to about 50N.

14. A method of treatment of a patient for opioid dependency and/or addiction, or for pain, which method comprises administering to said patient a pharmaceutical composition according to claim 8.

* * * * *